US007601532B2

(12) United States Patent
Nakagawara et al.

(10) Patent No.: US 7,601,532 B2
(45) Date of Patent: Oct. 13, 2009

(54) MICROARRAY FOR PREDICTING THE PROGNOSIS OF NEUROBLASTOMA AND METHOD FOR PREDICTING THE PROGNOSIS OF NEUROBLASTOMA

(75) Inventors: Akira Nakagawara, Chiba (JP); Miki Ohira, Chiba (JP); Shin Ishii, Ikoma (JP); Takeshi Goto, Tokyo (JP); Hiroyuki Kubo, Tokyo (JP); Takahiro Hirata, Tokyo (JP); Yasuko Yoshida, Nagoya (JP); Saichi Yamada, Ichinomiya (JP)

(73) Assignees: Hisamitsu Pharmaceutical Co., Inc., Tosu (JP); NGK Insulators, Ltd., Nagoya (JP); Chiba-Prefecture, Chiba (JP)

( * ) Notice: Subject to any disclaimer, the term of this patent is extended or adjusted under 35 U.S.C. 154(b) by 408 days.

(21) Appl. No.: 10/947,249

(22) Filed: Sep. 23, 2004

(65) Prior Publication Data

US 2005/0287541 A1 Dec. 29, 2005

Related U.S. Application Data

(60) Provisional application No. 60/505,614, filed on Sep. 25, 2003.

(51) Int. Cl.
| C12M 3/00 | (2006.01) |
| C12M 1/34 | (2006.01) |
| C07H 21/02 | (2006.01) |
| C07H 21/04 | (2006.01) |
| C12Q 1/68 | (2006.01) |

(52) U.S. Cl. .................. 435/287.2; 536/23.1; 536/24.3; 435/6

(58) Field of Classification Search ........................ None
See application file for complete search history.

(56) References Cited

U.S. PATENT DOCUMENTS

| 4,458,066 A | 7/1984 | Caruthers et al. |
| 5,474,796 A * | 12/1995 | Brennan ..................... 427/2.13 |
| 5,807,522 A | 9/1998 | Brown et al. |
| 6,582,908 B2 * | 6/2003 | Fodor et al. ..................... 435/6 |

FOREIGN PATENT DOCUMENTS

| JP | A-2001-116750 | 4/2001 |
| JP | A-2001-186880 | 7/2001 |
| JP | A-2001-186881 | 7/2001 |
| JP | A-2001-245671 | 9/2001 |
| JP | A-2001-321175 | 11/2001 |
| JP | A-2004-147563 | 5/2004 |
| WO | WO 01/66719 A1 | 9/2001 |
| WO | WO 01/66733 A1 | 9/2001 |
| WO | WO 03/038089 A1 | 5/2003 |

OTHER PUBLICATIONS

Sotiriou et al. Journal of Molecular Diagnoistics Feb. 2002 vol. 4 p. 30.*
Newton et al (Journal of Computational Biology 2001 vol. 8 p. 37).*
Wu (Journal of pathology 2001 vol. 195 p. 53).*
Cheung et al (Nature Genetics 2003 vol. 33 p. 422).*
Takita et al. (Genes, Chromosomes and Cancer 2004 vol. 40 p. 120).*
Ohira et al. (Cancer Cell Apr. 2005 vol. 7 p. 337).*

* cited by examiner

*Primary Examiner*—Sarae Bausch
*Assistant Examiner*—Katherine Salmon
(74) *Attorney, Agent, or Firm*—Oliff & Berridge, Plc

(57) ABSTRACT

A microarray for predicting the prognosis of neuroblastoma, wherein the microarray has 25 to 45 probes related to good prognosis, which are hybridized to a gene transcript whose expression is increased in a good prognosis patient with neuroblastoma and are selected from 96 polynucleotides consisting of the nucleotide sequences of SEQ. ID NOs. 1, 5, 6, 14, 16, 17, 19, 22-24, 28, 29, 31, 37, 39, 40, 43, 44, 47-52, 54, 57-60, 62, 64, 65, 67, 68, 72-75, 77, 78, 80-82, 84, 87, 89-91, 94, 100, 103, 112, 113, 118, 120, 129, 130, 132, 136, 138, 142, 144, 145, 148, 150-153, 155, 158-160, 163-165, 169-171, 173, 174, 177, 178, 180-182, 184, 186, 187, 189, 191, 192, 194, 195, 198-200 or their partial continuous sequences or their complementary strands, and 25 to 45 probes related to poor prognosis, which are hybridized to a gene transcript whose expression is increased in a poor prognosis patient with neuroblastoma and are selected from 104 polynucleotides consisting of the nucleotide sequences of SEQ. ID NOs. 2-4, 7-13, 15, 18, 20, 21, 25-27, 30, 32-36, 38, 41, 42, 45, 46, 53, 55, 56, 61, 63, 66, 69-71, 76, 79, 83, 85, 86, 88, 92, 93, 95-99, 101, 102, 104-111, 114-117, 119, 121-128, 131, 133-135, 137, 139-141, 143, 146, 147, 149, 154, 156, 157, 161, 162, 166-168, 172, 175, 176, 179, 183, 185, 188, 190, 193, 196, 197 or their partial continuous sequences or their complementary strands.

1 Claim, 13 Drawing Sheets

MICROARRAY FOR PREDICTING THE PROGNOSIS OF NEUROBLASTOMA AND METHOD FOR PREDICTING THE PROGNOSIS OF NEUROBLASTOMA

This nonprovisional application claims the benefit of U.S. Provisional Application No. 60/505,614, filed Sep. 25, 2003.

TECHNICAL FIELD

The invention of this application relates to a microarray for predicting the prognosis of neuroblastoma. More particularly, the invention of this application relates to a microarray for performing a molecular biological diagnosis of whether the prognosis of a patient with neuroblastoma after medical treatment is good or poor, and a method for predicting the prognosis of neuroblastoma using this microarray.

BACKGROUND ART

Neuroblastoma is one of the most common solid tumors in children and is originated from the sympathoadrenal lineage of the neural crest (Bolande, 1974: non-patent document 1). Its clinical behavior is heterogeneous: the tumors found in infants frequently regress spontaneously by inducing differentiation and/or programmed cell death, while those occurred in the patients over one year of age are often aggressive and acquire the resistance to intensive chemotherapy. Though the recent progress in the therapeutic strategies against advanced stages of neuroblastomas has improved the survival rate, the long-term results are still very poor. In addition, some of the tumors categorized to the intermediate group (in stage 3 or 4, and possessing a single copy of the MYCN gene) often recur after a complete response to the initial therapy. It is conceivable that such differences in the final outcome among the tumors maybe due to the differences in genetic and biological abnormalities which are reflected to the expression profile of genes and proteins in the tumor.

The prediction of the prognosis is one of the most emergent demands for starting the treatment of neuroblastoma. A patient's age (over or under one year of age), as expected from the natural history of neuroblastoma, is an important factor to segregate the outcome into favorable and unfavorable groups (Evans et al., 1971: non-patent document 2). The disease stage is also a powerful indicator of prognosis (Brodeur et al., 1993: non-patent document 3). Moreover, recent advances in basic research have found more than several molecular markers which are useful in the clinic. They include amplification of MYCN oncogene (Schwab et al., 1983: non-patent document 4; Brodeur et al., 1984: non-patent document 5), DNA ploidy (Look et al., 1984, 1991: non-patent document 6, 7), deletion of chromosome 1p (Brodeur et al., 1988: non-patent document 8) and TrkA expression (Nakagawara et al., 1992, 1993: non-patent document 9, 10), some of which are already used as prognostic indicators to choose the therapeutic strategy at the bedside. The other indicators also include telomerase (Hiyama et al., 1995: non-patent document 11), CD44 (Favrot et al., 1993: non-patent document 12), pleiotrophin (Nakagawara et al., 1995: non-patent document 13), N-cadherin (Shimono et al., 2000: non-patent document 14), CDC10 (Nagata et al., 2000: non-patent document 15), and Fyn (Berwanger et al., 2002: non-patent document 16). However, even their combination often fails to predict the patients' outcome. Therefore, new diagnostic tools in the postgenomic era have been expected to become available. Recently, DNA microarray method has been applied to comprehensively demonstrate expression profiles of primary neuroblastomas as well as cell lines. It has already identified several genes differentially expressed between favorable and unfavorable subsets (Yamanaka et al., 2002: non-patent document 17; Berwanger et al., 2002: non-patent document 16) or the genes changed during retinoic acid-induced neuronal differentiation (Ueda, 2001: non-patent document 18). However, the study to predict the prognosis by microarray using a large number of neuroblastoma samples has never been reported.

The present inventors have recently isolated 5,500 independent genes from the cDNA libraries generated from the primary neuroblastomas, a part of which has been previously reported (Ohira et al., 2003a, 2003b: non-patent document 19, 20). Further the present inventors have files patent applications relating to full disclosure of the isolated genes, and a relationship between the outcome predictability of neuroblastoma and the genes' expressions (patent documents 1-5)

Patent documents
1: JP 2001-245671A
2: JP 2001-321175A
3: PCT/JP01/01631 pamphlet
4: PCT/JP01/01629 pamphlet
5: JP2004-147563A Non-patent documents
1: Bolande, R. P. Hum Pathol 5, 409-429 (1974).
2: Evans, A. E. et al. Cancer 27, 374-8 (1971).
3: Brodeur, G. M. et al. J Clin Oncol 11, 1466-77 (1993).
4: Schwab, M. et al. Nature 305, 245-8 (1983).
5: Brodeur, G. M. et al. Science 224, 1121-4 (1984).
6: Look, A. T. et al. N Engl J Med 311, 231-5 (1984).
7: Look, A. T. et al. J Clin Oncol 9, 581-91 (1991).
8: Brodeur, G. M. et al. Prog Clin Biol Res 271, 3-15 (1988).
9: Nakagawara, A. et al. Cancer Res 52, 1364-8 (1992).
10: Nakagawara, A. et al. N Engl J Med 328, 847-54 (1993).
11: Hiyama, E. et al. Nat Med 1, 249-55 (1995).
12: Favrot, M. C. et al. N Engl J Med 329 (1993).
13: Nakagawara, A. et al. Cancer Res 55, 1792-7 (1995).
14: Shimono, R. et al. Anticancer Res 20, 917-23 (2000).
15: Nagata, T. et al. J Surg Res 92, 267-75 (2000).
16: Berwanger, B. et al. Cancer Cell 2, 377-86 (2002).
17: Yamanaka, Y. et al. Int Oncol 21, 803-7 (2002).
18: Ueda, K. Kurume Med J 48, 159-64 (2001).
19: Ohira, M. et al. Oncogene 22, 5526-36 (2003a).
20: Ohira, M. et al. Cancer Lett 197, 63-8 (2003b).

DISCLOSURE OF INVENTION

It is extremely important for selecting a better medical treatment method for a patient to accurately predict whether the prognosis after medical treatment of neuroblastoma is good or poor. So far, several molecular markers which are capable of performing such a prediction have been identified. However, even if such molecular markers were used alone or in combination, the prediction of diagnosis of neuroblastoma was not always accurate.

The invention of this application has been carried out in view of the circumstances as above, and makes it an object to provide a novel method capable of accurate and convenient prediction of the prognosis of neuroblastoma.

This application provides the following inventions in order to solve the foregoing problems.

A first invention is a microarray having 25 to 45 probes related to good prognosis, which are hybridized to a gene transcript whose expression is increased in a good prognosis patient with neuroblastoma and are selected from 96 polynucleotides consisting of the nucleotide sequences of SEQ. ID NOs. 1, 5, 6, 14, 16, 17, 19, 22-24, 28, 29, 31, 37, 39, 40, 43, 44, 47-52, 54, 57-60, 62, 64, 65, 67, 68, 72-75, 77, 78, 80-82, 84, 87, 89-91, 94, 100, 103, 112, 113, 118, 120, 129, 130, 132, 136, 138, 142, 144, 145, 148, 150-153, 155, 158-160, 163-165, 169-171, 173, 174, 177, 178, 180-182, 184, 186, 187, 189, 191, 192, 194, 195, 198-200 or their partial continuous sequences or their complementary strands, and 25 to 45 probes related to poor prognosis, which are hybridized to a gene transcript whose expression is increased in a poor prognosis patient with neuroblastoma and are selected from 104 polynucleotides consisting of the nucleotide sequences of SEQ. ID NOs. 2-4, 7-13, 15, 18, 20, 21, 25-27, 30, 32-36, 38, 41, 42, 45, 46, 53, 55, 56, 61, 63, 66, 69-71, 76, 79, 83, 85, 86, 88, 92, 93, 95-99, 101, 102, 104-111, 114-117, 119, 121-128, 131, 133-135, 137, 139-141, 143, 146, 147, 149, 154, 156, 157, 161, 162, 166-168, 172, 175, 176, 179, 183, 185, 188, 190, 193, 196, 197 or their partial continuous sequences or their complementary strands.

A second invention is a method for predicting prognosis of neuroblastoma using the microarray according to claim 1, wherein the method comprises:
(a) a step of labeling a gene transcript obtained from a tumor cell of a patient diagnosed as having neuroblastoma;
(b) a step of bringing the labeled gene transcript into contact with the microarray according to claim 1;
(c) a step of measuring the labeling signal of each of the gene transcripts hybridized to 25 to 45 probes related to good prognosis and 25 to 45 probes related to poor prognosis on the microarray, respectively, and determines that the prognosis of the patient is good if significant labeling signals for 25 or more of the probes related to good prognosis were obtained, and that the prognosis of the patient is poor if significant labeling signals for 25 or more of the probes related to poor prognosis were obtained.

In other words, the inventors of this application used a microarray capable of analyzing the expression of 5,340 genes specific to neuroblastoma (non-patent documents 19, 20, and patent document 1), and analyzed the expression of the 5,340 genes using mRNAs isolated from 136 patients with neuroblastoma as a target. In addition, the inventors constructed a kernel-based probabilistic classification model and found out that the probabilistic output thereof defines the molecular signature of neuroblastoma for prediction of the prognosis and that the analysis of the expression level of specific genes is superior to a conventional method using a known molecular marker as a target in terms of the prediction of the prognosis, thus this invention has been worked out.

Specifically, this invention predict good and poor prognosis of neuroblastoma using 200 genes shown in Table 1 as a target. In Table 1, No. 1 to 200 in the first row correspond to Seq. ID No. 1 to 200 of the sequence table, and measurement value with a control sequence and with water are shown respectively in No. 201 to 212 (the numerical values in the sixth to ninth rows, which will be explained later). With respect to Seq. ID No. 140, the nucleotide sequence from 1 to 977 is the 5' sequence of the gene named Nb1a2151 and the nucleotide sequence from 983 to 1869 is the 3' sequence thereof.

TABLE 1

| Seq. ID No. | Gene Name on Spot | Acc. No. (known genes UCSC etc) | UCSC Homology | UCSC Mapping | ranking 6/2 | pairwise F-value | pairwise F-value | logrank p-value | |
|---|---|---|---|---|---|---|---|---|---|
| 1 | gene022 | NM_002051 | GATA3 | 10p14 | 253 | 0.580 | F | 0.001971 | |
| 2 | gene052-1 | NM_005378 | MYCN | 2p24.3 | 20 | 0.784 | UF | 0.001253 | |
| 3 | gene053-1 | NM_005378 | MYCN | 2p24.3 | 46 | 0.750 | UF | 0.00133 | |
| 4 | gene056 | NM_000546 | TP53 | 17p13.1 | 66 | 0.721 | UF | 0.004087 | |
| 5 | gene071 | NM_000360 | TH | 11p15.5 | 60 | 0.723 | F | 0.000787 | |
| 6 | gene073 | NM_002529 | NTRK1 | 1q23.1 | 118 | 0.667 | F | 0.000002 | |
| 7 | Nbla00013 | NM_006098 | GNB2L1 | 5q35.3 | 25 | 0.772 | UF | 0.000006 | |
| 8 | Nbla00083 | BC010577 | GRN | 17q21.3 | 131 | 0.657 | UF | 0.147089 | o |
| 9 | Nbla00127 | U26710 | CBLB | 3q13.11 | 315 | 0.553 | UF | 0.001669 | |
| 10 | Nbla00138 | D83779 | KIAA0195 | 17q25.1 | 339 | 0.535 | UF | 0.052854 | o |
| 11 | Nbla00139 | BC006772 | RPS13 | 11p15.1 | 153 | 0.646 | UF | 0.000912 | o |
| 12 | Nbla00202 | NM_014347 | ZF5128 | 19q13.4 | 254 | 0.579 | UF | 0.020624 | |
| 13 | Nbla00214 | BC007512 | RPL18A | 19p13.1 | 31 | 0.762 | UF | 0.000002 | o |
| 14 | Nbla00217 | S72871 | GATA2 | 3q21.3 | 95 | 0.678 | F | 0.010245 | |
| 15 | Nbla00259 | NM_001010 | RPS6 | 9p22.1 | 163 | 0.638 | UF | 0.001715 | |
| 16 | Nbla00260 | NM_006082 | K-ALPHA-1 | 12q13.1 | 1 | 0.873 | F | 0.000003 | |
| 17 | Nbla00269 | NM_000787 | DBH | 9q34.2 | 57 | 0.724 | F | 0.00362 | |
| 18 | Nbla00332 | NM_001404 | EEF1G | 11q12.3 | 5 | 0.836 | UF | 0.000055 | |
| 19 | Nbla00347 | X59798 | CCND1 | 11q13.3 | 235 | 0.592 | F | 0.001629 | |
| 20 | Nbla00359 | AF083811 | MAD1L1 | 7p22.3 | 69 | 0.708 | UF | 0.00112 | |
| 21 | Nbla00383 | NM_001023 | RPS20 | 8q12.1 | 359 | 0.519 | UF | 0.056573 | |
| 22 | Nbla00391 | T09492 | AF036613 | 7q11.23 | 102 | 0.676 | F | 0.000539 | |
| 23 | Nbla00487 | NM_024909 | FLJ13158 | 6p21.33 | 47 | 0.745 | F | 0.002751 | |
| 24 | Nbla00488 | AK055378 | AK055378 | 17q21.1 | 165 | 0.636 | F | 0.00289 | |
| 25 | Nbla00501 | NM_000969 | RPL5, corresponding to intron | 1p22.1 | 15 | 0.786 | UF | 0.005786 | |
| 26 | Nbla00503 | NM_004793 | PRSS15, corresponding to intron | 19p13.3 | 91 | 0.679 | UF | 0.000169 | |
| 27 | Nbla00576 | BC016346 | FTL | 19q13.3 | 323 | 0.545 | UF | 0.215576 | o |
| 28 | Nbla00578 | NM_006818 | AF1Q | 1q21.3 | 79 | 0.690 | F | 0.009397 | |
| 29 | Nbla00610 | U03105 | PROL2 | 6q15 | 203 | 0.609 | F | 0.033502 | |
| 30 | Nbla00696 | X04098 | ACTG1 | 17q25.3 | 199 | 0.611 | UF | 0.10486 | |
| 31 | Nbla00715 | AF131776 | AF131776 | 7p13 | 273 | 0.575 | F | 0.000342 | |
| 32 | Nbla00754 | M17886 | RPLP1 | 15q23 | 123 | 0.657 | UF | 0.000068 | |
| 33 | Nbla00772 | NM_000681 | ADRA2A | 10q25.2 | 353 | 0.525 | UF | 0.022749 | |

TABLE 1-continued

| Seq. ID No. | Gene Name on Spot | Acc. No. (known genes UCSC etc) | UCSC Homology | UCSC Mapping | ranking 6/2 | pairwise F-value | pairwise F-value | logrank p-value | |
|---|---|---|---|---|---|---|---|---|---|
| 34 | Nbla00781 | BC009970 | TKT | 3p21.1 | 26 | 0.772 | UF | 0.048075 | o |
| 35 | Nbla00800 | D84294 | TTC3 | 21q22.1 | 311 | 0.554 | UF | 0.020169 | o |
| 36 | Nbla00824 | NM_003958 | RNF8 | 6p21.2 | 239 | 0.590 | UF | 0.004012 | |
| 37 | Nbla00890 | NM_003899 | ARHGEF7 | 13q34 | 62 | 0.721 | F | 0.000001 | |
| 38 | Nbla00901 | NM_005663 | WHSC2 | 4p16.3 | 83 | 0.689 | UF | 0.090789 | |
| 39 | Nbla02965 | X63432 | ACTB | 7p22.1 | 137 | 0.649 | F | 0.700325 | |
| 40 | Nbla02985 | NM_001386 | DPYSL2 | 8p21.2 | 275 | 0.571 | F | 0.005059 | |
| 41 | Nbla02990 | NM_006597 | HSPA8 | 11q24.1 | 221 | 0.600 | UF | 0.386365 | |
| 42 | Nbla03025 | NM_007103 | NDUFV1 | 11q13.2 | 73 | 0.696 | UF | 0.143343 | |
| 43 | Nbla03135 | BC045747 | BC045747 | 22q13.1 | 295 | 0.567 | F | 0.001318 | |
| 44 | Nbla03145 | NM_004826 | ECEL1 | 2q37.1 | 55 | 0.727 | F | 0.000494 | |
| 45 | Nbla03251 | AF078866 | SURF4 | 9q34.2 | 296 | 0.563 | UF | 0.015889 | |
| 46 | Nbla03286 | NM_020198 | GK001, AF226054 | 17q23.3 | 28 | 0.772 | UF | 0.000175 | |
| 47 | Nbla03323 | D78014 | DRYSL3 | 5q32 | 140 | 0.648 | F | 0.000019 | |
| 48 | Nbla03342 | X80199 | MLN51 | 17q21.1 | 212 | 0.603 | F | 0.000093 | |
| 49 | Nbla03401 | NM_004772 | C5orf13 | 5q22.1 | 299 | 0.563 | F | 0.00298 | |
| 50 | Nbla03430 | NM_007029 | STMN2 | 8q21.13 | 213 | 0.600 | F | 0.000276 | |
| 51 | Nbla03499 | NM_002074 | GNB1 | 1p36.33 | 33 | 0.762 | F | 0.000795 | |
| 52 | Nbla03518 | U14394 | TIMP3 | 22q12.3 | 119 | 0.667 | F | 0.000661 | |
| 53 | Nbla03521 | NM_032015 | RNF26 | 11q23.3 | 93 | 0.679 | UF | 0.010481 | |
| 54 | Nbla03533 | AK000237 | VAT1 | 17q21.3 | 182 | 0.629 | F | 0.20487 | |
| 55 | Nbla03534 | NM_005381 | NCL | 2q37.1 | 84 | 0.689 | UF | 0.015632 | |
| 56 | Nbla03604 | NM_001626 | AKT2 | 19q13.2 | 154 | 0.638 | UF | 0.05307 | |
| 57 | Nbla03646 | NM_014762 | DHCR24 | 1p32.3 | 289 | 0.571 | F | 0.010653 | |
| 58 | Nbla03651 | NM_003885 | CDK5R1 | 17q11.2 | 256 | 0.579 | F | 0.000002 | |
| 59 | Nbla03682 | NM_001843 | CNTN1 | 12q12 | 360 | 0.517 | F | 0.002928 | |
| 60 | Nbla03740 | NM_000615 | NCAM1 | 11q23.1 | 215 | 0.600 | F | 0.000002 | |
| 61 | Nbla03750 | L22557 | MGC8407 | 3p21.31 | 222 | 0.597 | UF | 0.256036 | |
| 62 | Nbla03755 | NM_005910 | MAPT | 17q21.3 | 208 | 0.605 | F | 0.000413 | |
| 63 | Nbla03761 | NM_014213 | HOXD9 | 2q31.1 | 330 | 0.543 | UF | 0.015653 | |
| 64 | Nbla03767 | AK025927 | MGC8721 | 8p12 | 75 | 0.694 | F | 0.000011 | |
| 65 | Nbla03819 | NM_000240 | MAOA | Xp11.3 | 257 | 0.579 | F | 0.001533 | |
| 66 | Nbla03836 | NM_000972 | RPL7A | 9q34.2 | 98 | 0.677 | UF | 0.048031 | |
| 67 | Nbla03873 | NM_006054 | RTN3 | 11q13.1 | 58 | 0.724 | F | 0.00001 | |
| 68 | Nbla03896 | BC022509 | SCG2 | 2q36.1 | 306 | 0.557 | F | 0.001898 | o |
| 69 | Nbla03899 | NM_001641 | APEX1 | 14q11.2 | 201 | 0.609 | UF | 0.02278 | |
| 70 | Nbla03925 | BC015654 | LAMR1 | 3p22.2 | 63 | 0.721 | UF | 0.001773 | o |
| 71 | Nbla03938 | NM_002948 | RPL15 | 3p24.2 | 244 | 0.588 | UF | 0.136289 | |
| 72 | Nbla03949 | BC011520 | STMN4 | 8p21.2 | 265 | 0.576 | F | 0.001411 | o |
| 73 | Nbla03954 | NM_000610 | CD44 | 11p13 | 141 | 0.647 | F | 0.000045 | |
| 74 | Nbla03969 | AB058781 | MAP6 | 11q13.5 | 223 | 0.597 | F | 0.000025 | |
| 75 | Nbla04104 | D00099 | ATP1A1 | 1p13.1 | 331 | 0.541 | F | 0.072373 | |
| 76 | Nbla04029 | NM_016091 | EIF3S6IP | 22q13.1 | 248 | 0.583 | UF | 0.05877 | |
| 77 | Nbla04134 | T13156 | MBC2 | 12q13.2 | 107 | 0.667 | F | 0.015693 | |
| 78 | Nbla04181 | AK055112 | AK055112 | 5q13.2 | 183 | 0.627 | F | 0.001425 | |
| 79 | Nbla04200 | BC007748 | RPL4 | 15q22.3 | 81 | 0.690 | UF | 0.04097 | o |
| 80 | Nbla04225 | NM_021814 | HELO1 | 6p12.1 | 258 | 0.579 | F | 0.061412 | |
| 81 | Nbla04269 | NM_006386 | DDX17 | 22q13.1 | 348 | 0.529 | F | 0.006945 | |
| 82 | Nbla04270 | AJ132695 | RAC1 | 7p22.1 | 173 | 0.633 | F | 0.012286 | |
| 83 | Nbla04293 | NM_002654 | PKM2 | 15q23 | 49 | 0.738 | UF | 0.001516 | |
| 84 | Nbla04314 | NM_003347 | UBE2L3 | 22q11.2 | 198 | 0.613 | F | 0.082094 | |
| 85 | Nbla04332 | NM_152344 | FLJ30656 | 17q21.3 | 341 | 0.532 | UF | 0.006093 | |
| 86 | Nbla10054 | NM_002520 | NPM1 | 5q35.1 | 82 | 0.690 | UF | 0.000104 | |
| 87 | Nbla10093 | NM_000183 | HADHB | 2p23.3 | 8 | 0.828 | F | 0.000018 | |
| 88 | Nbla10153 | AB062057 | TM4SF2 | Xp11.4 | 313 | 0.553 | UF | 0.262965 | o |
| 89 | Nbla10203 | NM_015342 | KIAA0073 | 5q12.3 | 147 | 0.647 | F | 0.009215 | |
| 90 | Nbla10275 | NM_002567 | PBP | 12q24.2 | 277 | 0.571 | F | 0.001161 | |
| 91 | Nbla10296 | U50733 | DCTN2 | 12q13.3 | 332 | 0.541 | F | 0.002154 | |
| 92 | Nbla10302 | NM_001428 | ENO1 | 1p36.23 | 3 | 0.857 | UF | 0.007702 | |
| 93 | Nbla10313 | NM_002300 | LDHB = 3', chimera | (f = 7q21.11), 12p12.1 | 109 | 0.667 | UF | 0.12083 | |
| 94 | Nbla10327 | NM_014868 | RNF10 | 12q24.3 | 191 | 0.618 | F | 0.002878 | |
| 95 | Nbla10371 | NM_005370 | MEL | 19p13.1 | 192 | 0.615 | UF | 0.712687 | |
| 96 | Nbla10393 | NM_005412 | SHMT2 | 12q13.3 | 365 | 0.517 | UF | 0.106676 | |
| 97 | Nbla10395 | NM_002593 | PCOLCE | 7q22.1 | 110 | 0.667 | UF | 0.000164 | |
| 98 | Nbla10398 | NM_004713 | SDCCAG1 | 14q21.3 | 142 | 0.647 | UF | 0.012774 | |
| 99 | Nbla10400 | NM_014225 | PPP2R1A | 19q13.4 | 184 | 0.627 | UF | 0.112705 | |
| 100 | Nbla10441 | NM_003611 | OFD1 | Xp22.22 | 337 | 0.537 | F | 0.005758 | |
| 101 | Nbla10472 | NM_006666 | RUVBL2 | 19q13.3 | 158 | 0.638 | UF | 0.018914 | |
| 102 | Nbla10497 | NM_005275 | GNL1 | 6p21.33 | 278 | 0.571 | UF | 0.086044 | |
| 103 | Nbla10516 | BC016867 | TSC22 | 13q14.1 | 351 | 0.526 | F | 0.015244 | o |
| 104 | Nbla10530 | U01038 | PLK | 16p12.2 | 343 | 0.532 | UF | 0.001388 | |

TABLE 1-continued

| Seq. ID No. | Gene Name on Spot | Acc. No. (known genes UCSC etc) | UCSC Homology | UCSC Mapping | ranking 6/2 | pairwise F-value | pairwise F-value | logrank p-value | |
|---|---|---|---|---|---|---|---|---|---|
| 105 | Nbla10579 | AB002334 | AF432211 | 2q12.3 | 16 | 0.786 | UF | 0.000962 | |
| 106 | Nbla10671 | NM_003707 | RUVBL1 | 3q21.3 | 100 | 0.676 | UF | 0.052258 | |
| 107 | Nbla10727 | AK055935 | AK055935 | 17q25.1 | 349 | 0.528 | UF | 0.000198 | |
| 108 | Nbla10765 | NM_001168 | BIRC5 | 17q25.3 | 237 | 0.590 | UF | 0.000426 | |
| 109 | Nbla10788 | X02152 | LDHA | 11p15.1 | 303 | 0.559 | UF | 0.014818 | o |
| 110 | Nbla10836 | AF006043 | PHGDH | 1p12? | 187 | 0.627 | UF | 0.002437 | o |
| 111 | Nbla10849 | NM_002823 | PTMA | 2q37.1 | 290 | 0.567 | UF | 0.022365 | |
| 112 | Nbla10851 | BC004975 | CCNI | 4q21.1 | 159 | 0.638 | F | 0.009974 | o |
| 113 | Nbla10856 | AF026402 | U5-100K | 12q13.1 | 74 | 0.696 | F | 0.074918 | |
| 114 | Nbla10873 | NM_005762 | TRIM28 | 19q13.4 | 48 | 0.745 | UF | 0.004984 | |
| 115 | Nbla10925 | AB082924 | RPL13A | 19q13.3 | 111 | 0.667 | UF | 0.021005 | o |
| 116 | Nbla11013 | NM_000998 | RPL37A | 2q35 | 204 | 0.605 | UF | 0.059121 | |
| 117 | Nbla11084 | AF226604 | SR-BP1 | 9p13.3 | 148 | 0.646 | UF | 0.013851 | o |
| 118 | Nbla11092 | AK021601 | FLJ11539 | 4q34.1 | 307 | 0.554 | F | 0.225491 | |
| 119 | Nbla11148 | BC003655 | RPLP0 | 12q24.2 | 14 | 0.800 | UF | 0.000049 | o |
| 120 | Nbla11212 | AK001024 | FLJ10162 | 14q22.1 | 350 | 0.526 | F | 0.000039 | |
| 121 | Nbla11280 | NM_000984 | RPL23A | 17q11.2 | 263 | 0.579 | UF | 0.120135 | |
| 122 | Nbla11337 | NM_004487 | GOLGB1 | 3q21.1–q13.33 | 291 | 0.567 | UF | 0.032809 | |
| 123 | Nbla11400 | NM_001235 | SERPINH1 | 11q13.5 | 314 | 0.553 | UF | 0.125758 | |
| 124 | Nbla11459 | X70649 | DDX1 | 2p24.3 | 6 | 0.836 | UF | 0.000024 | o |
| 125 | Nbla11536 | NM_002394 | SLC3A2 | 11q12.3 | 112 | 0.667 | UF | 0.000897 | |
| 126 | Nbla11561 | NM_005742 | P5 | 2p25.1 | 308 | 0.554 | UF | 0.299715 | |
| 127 | Nbla11584 | J00231 | IGHG3 | 14q32.3 | 346 | 0.532 | UF | 0.151893 | o |
| 128 | Nbla11602 | NM_024034 | GDAP1L1 | 20q13.1 | 169 | 0.635 | UF | 0.357468 | |
| 129 | Nbla11606 | AF141347 | TUBA3 | 12q13.1 | 17 | 0.786 | F | 0 | o |
| 130 | Nbla11662 | NM_006761 | YWHAE | 17p13.3 | 120 | 0.667 | F | 0.00009 | |
| 131 | Nbla11732 | U14966 | RPL5 | 1p22.1 | 76 | 0.694 | UF | 0.001 | o |
| 132 | Nbla11788 | BC032703 | PRPH | 12q13.1 | 18 | 0.786 | F | 0.000017 | o |
| 133 | Nbla11890 | NM_001402 | EEF1A1 | 6q13 | 89 = 319 | 0.688 | UF | 0.191622 | |
| 134 | Nbla11919 | BC000502 | RPL17 | 18q21.1 | 280 | 0.571 | UF | 0.002429 | o |
| 135 | Nbla11970 | NM_002136 | HNRPA1 | 12q13.1 | 121 | 0.667 | UF | 0.001383 | |
| 136 | Nbla11993 | NM_015980 | HMP19 | 5q35.2 | 9 | 0.824 | F | 0.204274 | |
| 137 | Nbla12021 | BC007945 | RPS11 | 19q13.3 | 177 | 0.629 | UF | 0.005294 | o |
| 138 | Nbla12044 | Z48950 | H3F3B | 17q25.1 | 178 | 0.629 | F | 0.019723 | |
| 139 | Nbla12061 | AK055935 | AK055935 | 17q25.1 | 104 | 0.676 | UF | 0.000351 | |
| 140 | Nbla12151 | AU254033 AU254034 | LPIN1 intron, may be not | 2p25.1 | 281 | 0.571 | UF | 0.388543 | o |
| 141 | Nbla12165 | NM_001728 | BSG | 19p13.3 | 210 | 0.603 | UF | 0.015224 | |
| 142 | Nbla20089 | NM_006363 | SEC23B | 20p11.2 | 36 | 0.762 | F | 0.000764 | |
| 143 | Nbla20164 | NM_024827 | HDAC11 | 3p25.1 | 228 | 0.597 | UF | 0.023978 | |
| 144 | Nbla20393 | NM_021136 | RTN1 | 14q23.1 | 282 | 0.571 | F | 0.007075 | |
| 145 | Nbla20490 | AK125587 | AK125587 | 12q13.1 | 114 | 0.667 | F | 0.000013 | |
| 146 | Nbla20509 | NM_003016 | SFRS2 | 17q25.1 | 259 | 0.579 | UF | 0.105982 | |
| 147 | Nbla20562 | NM_001636 | SLC25A6 | Xp22.33 | 149 | 0.646 | UF | 0.001187 | |
| 148 | Nbla20713 | NM_021973 | HAND2? | 4q34.1 | 170 | 0.633 | F | 0.07252 | |
| 149 | Nbla20730 | AK027759 | AK027759 | 6q16.2 | 283 | 0.571 | UF | 0.050407 | |
| 150 | Nbla20771 | NM_002792 | PSMA7 | 20q13.3 | 251 | 0.581 | F | 0.44511 | |
| 151 | Nbla20790 | NM_002933 | RNASE1 | 14q11.2 | 316 | 0.551 | F | 0.04873 | |
| 152 | Nbla21270 | NM_001915 | CYB561 alternative form? | 17q23.3 | 44 | 0.750 | F | 0.00016 | |
| 153 | Nbla21298 | NM_144967 | FLJ30058 | Xq26.1 | 189 | 0.618 | F | 0.100113 | |
| 154 | Nbla21322 | NM_000175 | GPI | 19q13.1 | 333 | 0.541 | UF | 0.009434 | |
| 155 | Nbla21394 | NM_000743 | CHRNA3 | 15q25.1 | 64 | 0.721 | F | 0.072464 | |
| 156 | Nbla21432 | NM_000034 | ALDOA | 16p11.2 | 284 | 0.571 | UF | 0.04041 | |
| 157 | Nbla21595 | NM_004499 | HNRPAB | 5q35.3 | 336 | 0.541 | UF | 0.007699 | |
| 158 | Nbla21642 | NM_003487 | TAF15 | 17q12 | 231 | 0.597 | F | 0.001076 | |
| 159 | Nbla21784 | NM_002276 | KRT19 | 17q21.2 | 136 | 0.655 | F | 0.000015 | |
| 160 | Nbla21844 | NM_138394 | LOC92906 | 2p22.1 | 124 | 0.657 | F | 0.000082 | |
| 161 | Nbla21852 | NM_006034 | TP53I11 intron | 11p11.2 | 267 | 0.575 | UF | 0.010103 | |
| 162 | Nbla21871 | NM_001129 | AEBP1 | 7p13 | 352 | 0.525 | UF | 0.129418 | |
| 163 | Nbla21891 | NM_014396 | VPS41 | 7p14.1 | 19 | 0.784 | F | 0.000006 | |
| 164 | Nbla21984 | NM_005386 | NNAT | 20q11.2 | 234 | 0.595 | F | 0.025244 | |
| 165 | Nbla22156 | NM_014944 | CLSTN1 | 1p36.22 | 50 | 0.738 | F | 0.005233 | |
| 166 | Nbla22328 | NM_005507 | CFL1 | 11q13.1 | 334 | 0.541 | UF | 0.008023 | |
| 167 | Nbla22411 | NM_015665 | AAAS | 12q13.1 | 324 | 0.543 | UF | 0.044806 | |
| 168 | Nbla22424 | NM_004375 | COX11 | 17q22 | 217 | 0.600 | UF | 0.305225 | |
| 169 | Nbla22426 | NM_145900 | HMGA1 | 6p21.31 | 304 | 0.557 | F | 0.163535 | |
| 170 | Nbla22510 | NM_016250 | NDRG2 | 14q11.2 | 262 | 0.579 | F | 0.028274 | |
| 171 | Nbla22531 | NM_002045 | GAP43 | 3q13.31 | 24 | 0.776 | F | 0.004394 | |
| 172 | Nbla22554 | NM_000687 | AHCY | 20q11.2 | 65 | 0.721 | UF | 0.003946 | |

TABLE 1-continued

| Seq. ID No. | Gene Name on Spot | Acc. No. (known genes UCSC etc) | UCSC Homology | UCSC Mapping | ranking 6/2 | pairwise F-value | pairwise F-value | logrank p-value | |
|---|---|---|---|---|---|---|---|---|---|
| 173 | Nbla22572 | NM_000790 | DDC | 7p12.2 | 41 | 0.754 | F | 0.000035 | |
| 174 | Nbla22633 | NM_080607 | C20orf102 | 20q11.2 | 317 | 0.551 | F | 0.002731 | |
| 175 | Nbla22643 | NM_017705 | FLJ20190 | 15q23 | 115 | 0.667 | UF | 0.046801 | |
| 176 | Nbla22960 | NM_021131 | PPP2R4 | 9q34.11 | 318 | 0.551 | UF | 0.053406 | |
| 177 | Nbla22997 | NM_005389 | PCMT1 | 6q25.1 | 310 | 0.554 | F | 0.00074 | |
| 178 | Nbla23003- | NM_001281 | CKAP1 | 19q13.1 | 321 | 0.551 | F | 0.50794 | |
| 179 | Nbla23007 | NM_021939 | FKBP10 | 17q21.2 | 90 | 0.687 | UF | 0.069405 | |
| 180 | Nbla23017 | NM_007178 | UNRIP | 12p12.3 | 326 | 0.543 | F | 0.028015 | |
| 181 | Nbla23089 | NM_014232 | VAMP2 | 17p13.1 | 132 | 0.655 | F | 0.001788 | |
| 182 | Nbla23144 | NM_014841 | SNAP91 | 6q14.2 | 264 | 0.576 | F | 0.000026 | |
| 183 | Nbla23163 | NM_003754 | EIF3S5 | 11p15.4 | 42 | 0.754 | UF | 0.000341 | |
| 184 | Nbla23178 | NM_004627 | WRB | 21q22.2 | 270 | 0.575 | F | 0.000244 | |
| 185 | Nbla23181 | NM_080725 | C20orf139 | 20p13 | 338 | 0.535 | UF | 0.108356 | |
| 186 | Nbla23325 | NM_003275 | TMOD1 | 9q22.33 | 205 | 0.605 | F | 0.000088 | |
| 187 | Nbla23420 | NM_173798 | LOC170261 | Xq24 | 206 | 0.605 | F | 0.000033 | |
| 188 | Nbla23424 | NM_001404 | EEF1G | 11q12.3 | 45 | 0.750 | UF | 0.003579 | |
| 189 | Nbla23443 | NM_014718 | CLSTN3 | 12p13.3 | 167 | 0.635 | F | 0.000234 | |
| 190 | Nbla23458 | NM_005053 | RAD23A | 19p13.2 | 358 | 0.521 | UF | 0.143918 | |
| 191 | Nbla23525 | BC035249 | BC035249 | Xq22.2 | 70 | 0.708 | F | 0.000003 | |
| 192 | Nbla23668 | AB028962 | KIAA1039 | 17p13.3 | 224 | 0.597 | F | 0.000634 | |
| 193 | Nbla23741 | NM_002404 | MFAP4 | 17p11.2 | 354 | 0.521 | UF | 0.005134 | |
| 194 | Nbla23949- | NM_015331 | NCSTN | 1q23.2 | 219 | 0.600 | F | 0.056869 | |
| 195 | Nbla24098 | NM_003127 | SPTAN1 | 9q34.11 | 144 | 0.647 | F | 0 | |
| 196 | Nbla24174 | NM_000521 | HEXB | 5q13.3 | 322 | 0.545 | UF | 0.273185 | |
| 197 | Nbla24848 | NM_017722 | FLJ20244 | 19p13.2 | 168 | 0.635 | UF | 0.015188 | |
| 198 | Nbla24920 | NM_006266 | RALGDS | 9q34.2 | 220 | 0.600 | F | 0.007387 | |
| 199 | Nbla24963 | NM_005517 | HMGN2 | 1p36.11 | 180 | 0.629 | F | 0.022671 | |
| 200 | Nbla24987 | NM_001978 | EPB49 | 8p21.3 | 196 | 0.615 | F | 0.004811 | |
| 201 | gene033-1 | | | | 363 | 0.513 | | 0.016162 | control |
| 202 | gene033-1 | | | | 363 | 0.513 | | 0.016162 | control |
| 203 | gene033-1 | | | | 363 | 0.513 | | 0.016162 | control |
| 204 | gene033-1 | | | | 363 | 0.513 | | 0.016162 | control |
| 205 | gene019-1 | | | | 125 | 0.657 | | 0.47227 | control |
| 206 | gene019-1 | | | | 125 | 0.657 | | 0.47227 | control |
| 207 | gene019-1 | | | | 125 | 0.657 | | 0.47227 | control |
| 208 | gene019-1 | | | | 125 | 0.657 | | 0.47227 | control |
| 209 | H2O | | | | | 0.000 | — | | control |
| 210 | H2O | | | | | 0.000 | — | | control |
| 211 | H2O | | | | | 0.000 | — | | control |
| 212 | H2O | | | | | 0.000 | — | | control |

In this invention, "polynucleotide" is referred to as a molecule in which a plural of, preferably not less than 30 phosphate esters of nucleosides in which a purine or a pyrimidine is attached to a sugar via a β-N-glycosidic bond (ATP, GTP, CTP, UTP, DATP, dGTP, dCTP or dTTP) are bound to one another. "Gene transcript" is referred to as a mRNA transcribed from genomic gene or a cDNA synthesized from this mRNA.

"Predicting prognosis" means to predict whether the postoperative status of a patient with neuroblastoma is good or poor. More specifically, the "good prognosis" indicates the status in which a neuroblastoma is localized or regressed, or it becomes a benign sympathetic ganglion cell tumor. Examples include the case where the patient is alive 5 years or more after the operation without recurrence. The "poor prognosis" indicates the status in which the progression of neuroblastoma is confirmed, and examples include the status where there is a risk that the patient will die within 3 years after the operation.

Other terms and concepts in this invention will be defined in detail in the description of the embodiments or Examples of the invention. The terms are basically in accordance with IUPAC-IUB Commission on Biochemical Nomenclature or the meanings of terms used commonly in the art. In addition, various techniques used for implementing the invention can be easily and surely carried out by those skilled in the art based on a known literature or the like except for the techniques whose sources are particularly specified. For example, techniques of genetic engineering and molecular biology can be carried out according to the methods described in J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vol. 1 to 4, (The Practical Approach Series), IRL Press, Oxford University Press (1995); Ausubel, F. M. et al., Current Protocols in Molecular Biology, John Wiley & Sons, New York, N.Y, 1995; Japanese Biochemical Society ed., "Zoku Seikagaku Jikken Koza 1, Idenshi Kenkyuho II" Tokyo Kagaku Dozin (1986); Japanese Biochemical Society ed., "Shin Seikagaku Jikken Koza 2, Kakusan III (Kumikae DNA Gijutsu)" Tokyo Kagaku Dozin (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987), etc. or the methods described in the references cited therein or substantially the same methods or the modifications thereof.

BEST MODE FOR CARRYING OUT THE INVENTION

Figure 1:
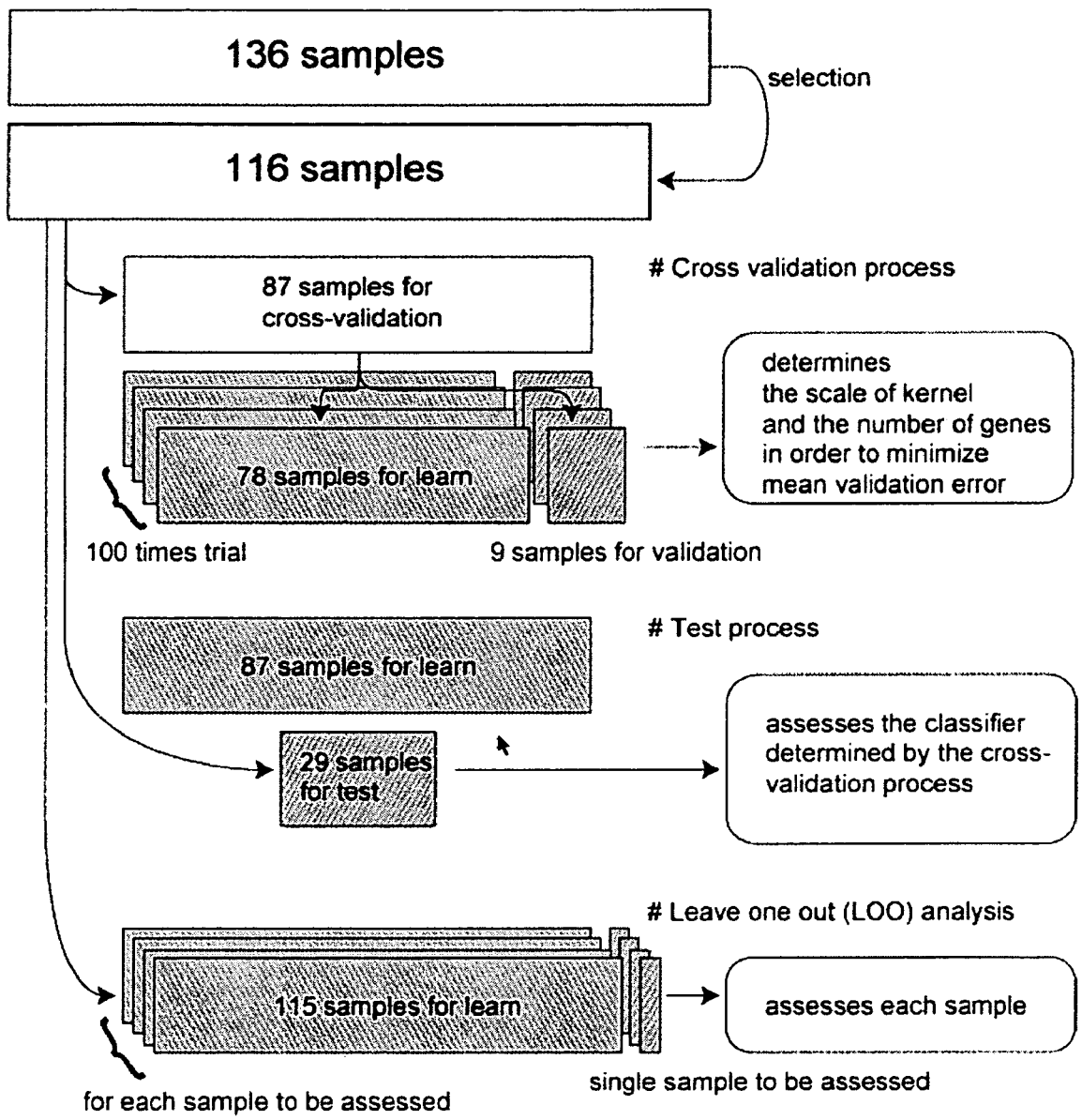
FIG. 1 is a schematic representation of machine learning and cross validation. Originally 136 patient samples were prepared. All of them were used in the Kaplan-Meier analysis. In the subsequent supervised classification analysis, 116 samples whose prognosis was known at 24 month after diagnosis were used. 116 samples were divided into 87 samples for cross-validation and 29 samples for the final test. In the cross-validation analysis, the outcome of randomly selected 9 samples are predicted by a classifier constructed from the rest 78 samples, and repeated this process 100 times by varying the set of 9 samples. The scale parameter of the Gaussian kernel and the number of genes were determined so as to minimize the mean prediction error (validation error). The classifier using those parameter values was assessed by the 29 samples as the final test. 116 samples were also assessed again by leave-one-out (LOO) analysis.

Each of the polynucleotides consisting of the nucleotide sequences of SEQ. ID NOs. 1, 5, 6, 14, 16, 17, 19, 22-24, 28, 29, 31, 37, 39, 40, 43, 44, 47-52, 54, 57-60, 62, 64, 65, 67, 68, 72-75, 77, 78, 80-82, 84, 87, 89-91, 94, 100, 103, 112, 113, 118, 120, 129, 130, 132, 136, 138, 142, 144, 145, 148, 150-153, 155, 158-160, 163-165, 169-171, 173, 174, 177, 178, 180-182, 184, 186, 187, 189, 191, 192, 194, 195, 198-200 is a cDNA of each of the specific 96 genes (see Table 1) whose expression is increased in a good prognosis patient with neuroblastoma. Each of the polynucleotides of SEQ. ID NOs. 2-4, 7-13, 15, 18, 20, 21, 25-27, 30, 32-36, 38, 41, 42, 45, 46, 53, 55, 56, 61, 63, 66, 69-71, 76, 79, 83, 85, 86, 88, 92, 93, 95-99, 101, 102, 104-111, 114-117, 119, 121-128, 131, 133-135, 137, 139-141, 143, 146, 147, 149, 154, 156, 157, 161, 162, 166-168, 172, 175, 176, 179, 183, 185, 188, 190, 193, 196, 197 is a cDNA of each of the specific 104 genes (see Table 1) whose expression is increased in a poor prognosis patient with neuroblastoma. The microarray of the first invention is a microarray having probes related to good prognosis, which are hybridized to each of the 25 to 45 types among 96 genes related to good prognosis, and probes related to poor prognosis, which are hybridized to each of the 25 to 45 types among 104 gene transcripts related to poor prognosis. In other words, this microarray has 50 to 90 types, preferably 60 to 80 types, more preferably 65 to 75 types of probes which are hybridized to each of the total of 200 types of gene transcripts related to good prognosis and poor prognosis. Incidentally, from the results of the Examples described later, 70 genes (33 genes related to good prognosis and 37 genes related to poor prognosis) shown in Table 2 are illustrated as a preferred test target, however, the microarray of this invention is not intended to be limited to using these genes as a target. It will be easily conceived by those skilled in the art that the number and the types of probes can be determined by, for example, selecting more preferred target genes as needed from the results obtained by the diagnostic method of the second invention (see the Examples described later), the results of the subsequent follow-up study on the patient and the like.

With respect to the probes for the microarray of the first invention, for example, in the case where RNAs (mRNAs) of respective genes related to good prognosis and poor prognosis are used as a target, respective cDNAs of SEQ. ID NOs. 1, 5, 6, 14, 16, 17, 19, 22-24, 28, 29, 31, 37, 39, 40, 43, 44, 47-52, 54, 57-60, 62, 64, 65, 67, 68, 72-75, 77, 78, 80-82, 84, 87, 89-91, 94, 100, 103, 112, 113, 118, 120, 129, 130, 132, 136, 138, 142, 144, 145, 148, 150-153, 155, 158-160, 163-165, 169-171, 173, 174, 177, 178, 180-182, 184, 186, 187, 189, 191, 192, 194, 195, 198-200 and SEQ. ID NOs. 2-4, 7-13, 15, 18, 20, 21, 25-27, 30, 32-36, 38, 41, 42, 45, 46, 53, 55, 56, 61, 63, 66, 69-71, 76, 79, 83, 85, 86, 88, 92, 93, 95-99, 101, 102, 104-111, 114-117, 119, 121-128, 131, 133-135, 137, 139-141, 143, 146, 147, 149, 154, 156, 157, 161, 162, 166-168, 172, 175, 176, 179, 183, 185, 188, 190, 193, 196, 197 or their partial continuous sequences (for example, about 15 to 50 bp) may be used as the probes. In addition, in the case where cDNAs of genes related to good prognosis and poor prognosis are used as a target for detection, complementary polynucleotide strands for the respective cDNAs may be used as the probes.

As the cDNA probe for targeting a gene mRNA, for example, a full length cDNA prepared by a known method (Mol. Cell. Biol. 2, 167-170,1982; J. Gene 25, 263-269, 1983; Gene, 150, 243-250, 1994) using poly(A)+RNA extracted from a human cell as a template can be used. Also, it can be synthesized by the RT-PCR method using a mRNA isolated from a human cell as a template and using a primer set designed based on the information of the nucleotide sequences of Seq. ID No. 1 to 200. Further, a target full length cDNA can be synthesized by synthesizing partial sequences with a DNA oligo synthesizer and ligating them by an enzymatic method and a subcloning method. In addition, in the case where a polynucleotide consisting of a partial continuous sequence of a cDNA is used as a probe, an objective short-chain cDNA can be prepared by a method of digesting the obtained full length cDNA with an appropriate restriction enzyme or by a DNA oligo synthesizer or a known chemical synthesis technique (for example, Carruthers (1982) Cold Spring Harbor Symp. Quant. Biol. 47: 411-418; Adams (1983) J. Am. Chem. Soc. 105: 661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68:109; Beaucage (1981) Tetra. Lett. 22: 1859; U.S. Pat. No. 4,458,066).

On the other hand, a probe in the case of targeting a cDNA synthesized from a gene mRNA is a complementary polynucleotide for a full length or a partial continuous sequence of respective cDNAs, and can be prepared by the same DNA oligo synthesizer or known chemical synthesis technique as described above.

The microarray of the first invention uses the probes as described above and can be prepared in the same manner as a common DNA microarray. As a method of preparing the microarray, a method of synthesizing the probes directly on the surface of a solid phase support (on-chip method) and a method of immobilizing the probes prepared in advance on the surface of a solid phase substrate are known, however, it is preferred that the microarray of this invention be prepared by the latter method. In the case where the probes prepared in advance are immobilized on the surface of a solid phase substrate, a probe in which a functional group was introduced is synthesized, the probe is spotted on the surface of the solid phase substrate subjected to a surface treatment, and have it covalently bound thereto (for example, Lamture, J. B. et al. Nucl. Acids Res. 22: 2121-2125, 1994; Guo, Z. et al. Nucl. Acids Res. 22:5456-5465, 1994). In general, the probe is covalently bound to the solid phase substrate subjected to a surface treatment via a spacer or a crosslinker. A method of aligning small pieces of polyacrylamide gel on the surface of glass and having the probe covalently bound thereto (Yershov, G. et al. Proc. Natl. Acad. Sci. USA 94: 4913, 1996), or a method of binding the probe to the solid phase substrate coated with poly L-lysine (JP 2001-186880A) are also known. In addition, a method of preparing an array of microelectrode on a silica microarray, in which a permeation layer of agarose containing streptavidin is provided on the electrode to make it a reactive region, immobilizing a biotinylated probe by positively charging this region and controlling the electric charge of the region, thereby enabling high-speed and stringent hybridization is also known (Sosnowski, R. G. et al. Proc. Natl. Acad. Sci. USA 94: 1119-1123, 1997). The microarray of this invention can be prepared by any one of the foregoing methods. In the case where the probe is dropped on the surface of the solid phase substrate to perform spotting, it can be performed by a pin system (for example, U.S. Pat. No. 5,807,5223), however, it is preferred that an inkjet system disclosed in JP 2001-116750A or JP 2001-186881A be adopted because uniform spots in a specific shape are formed. In addition, this inkjet system can make the number of probes contained in the respective probe spots equal, therefore, the difference in hybridization due to the difference in the probe length can be accurately measured. Further, it is recommended for forming preferred spots that spotting be repeated as disclosed in JP 2001-186880A, or a probe solution (a solution containing a moisturizing substance) comprising the composition disclosed in WO 03/038089 A1 be used.

After the spotting, each spot is immobilized on the solid phase substrate by cooling, adding moisture to the spots (maintaining a humidity of up to about 80% for a given period of time) and performing such as an immobilization treatment or the like by calcination and drying, whereby the microarray can be completed.

As the solid phase substrate for the microarray, other than glass (slide glass) used for a common microarray, plastic, silicone, ceramic or the like can be also used.

The prediction of the prognosis of neuroblastoma of the second invention is carried out by using the foregoing microarray. In other words, this diagnostic method is a method comprising the following steps (a) to (c):
(a) a step of labeling a gene transcript obtained from a tumor cell of a patient diagnosed as having neuroblastoma;
(b) a step of bringing the labeled gene transcript into contact with the microarray according to claim 1;
(c) a step of measuring the labeling signal of each of the gene transcripts hybridized to 25 to 45 probes related to good prognosis and 25 to 45 probes related to poor prognosis on the microarray, respectively.

For example, in the case where the gene transcript to become a target for detection is a cDNA, a cDNA is prepared as a PCR product from a genomic gene isolated from an examinee or total RNAs in the step (a). During the PCR amplification, the cDNA is labeled by incorporating a labeling primer (for example, a primer to which a cyanine organic dye such as Cy3 or Cy5 was attached) thereinto. In the step (b), the targeting cDNA is brought into contact with the microarray to be hybridized to the probe on the microarray. In the case where the gene transcript to become a target for detection is a mRNA, total RNAs extracted from the cells of an examinee are labeled by using a commercially available labeling kit (for example, CyScribe™ RNA labeling kit: manufactured by Amersham Pharmacia Biotech Co.) or the like.

Hybridization in the step (b) can be carried out by spotting an aqueous solution of the labeled cDNA dispensed on a 96-well or 384-well plastic plate on the microarray. The amount to be spotted can be about 1 to 100 nl. It is preferred that hybridization be carried out at a temperature from room temperature up to 70° C. for 1 to 20 hours. After finishing the hybridization, washing is carried out by using a mixed solution of a surfactant and a buffer solution to remove unreacted labeled polynucleotides. As the surfactant, it is preferred that sodium dodecyl sulfate (SDS) be used. As the buffer solution, citrate buffer solution, phosphate buffer solution, borate buffer solution, Tris buffer solution, Good's buffer solution or the like can be used, however, it is preferred that citrate buffer solution be used. In the step (c), the signal obtained by the labeled gene product hybridized to the probe is measured.

The diagnostic method of the second method determines from the signal obtained as above that the prognosis of the patient is good if significant labeling signals for 25 or more (25 to 45, preferably 30 to 40, more preferably 32 to 38) of the probes related to good prognosis were obtained, and that the prognosis of the patient is poor if significant labeling signals for 25 or more (25 to 45, preferably 30 to 40, more preferably 32 to 38) of the probes related to poor prognosis were obtained.

Hereunder, this invention will be explained in detail by showing as the Examples the experimental results of identifying the target genes for the microarray or the diagnostic method of this invention, however, this invention is not intended to be limited to the following examples.

EXAMPLES

1. Materials and Methods 1-1. Patients and Tumor Specimens

Fresh, frozen tumor tissues were sent to the Division of Biochemistry, Chiba Cancer Center Research Institute, from a number of hospitals in Japan. The informed consents were obtained in each institution or hospital. Most of the samples were resected by pre-operational biopsy or surgery, without treatment by chemotherapy or radiotherapy. After the operation, patients were treated according to previously described common protocols (Kaneko, M. et al. Med. Pediatr Oncol 31, 1-7 (1998)). Biological information on each tumor including MYCN gene copy number, TrkA gene expression, and DNA ploidy, was analyzed in our laboratory. All tumors were classified according to the International Neuroblastoma Staging System (INSS): stages 1 and 2, localized neuroblastomas; stages 3 and 4, locally and regionally growing and distantly metastatic neuroblastomas; and stage 4s, neuroblastomas in children under one year of age, with metastases restricted to skin, liver, and bone marrow, usually regressing spontaneously (Brodeur et al., 1993: non-patent document 3).

In Japan, a mass screening program for infants at the age of 6 months has been performed since 1985. Patients found by this screening have been mostly classified to the early stage of the disease, although a small proportion had unfavorable prognoses (Sawada et al., Lancet 2, 271-3 (1984)). Among the 136 tumors of being analyzed, 68 of those were found by this screening. All diagnoses of neuroblastoma were confirmed by histological assessment of a surgery resected tumor specimen.

Frozen tissues were homogenized in guanidinium isothiocyanate, and total RNA was extracted from each sample using the AGPC method (Chomczynski and Sacchi, Anal Biochem 162, 156-9 (1987)). RNA integrity, quality, and quantity were then assessed by electrophoresis on Agilent RNA 6000 nano chip using Agilent 2100 BioAnalyzer (Agilent Technologies, Inc.).

1-2. cDNA Microarray Experiments

To make a neuroblastoma-specific cDNA microarray (named as CCC-NB5000-Chip ver.1), 5,340 cDNA clones were selected from –10,000 of those isolated from three types of neuroblastoma oligo-capping cDNA libraries (favorable, unfavorable and stage 4s neuroblastomas) after a removal of highly duplicated genes. Insert DNAs were amplified by polymerase chain reaction (PCR) from these cDNA clones, purified by ethanol precipitation, and spotted onto a glass slide in a high density manner by an ink-jet printing tool (NGK insulators, Ltd.). Additional 80 cDNAs that had been described as candidates for prognostic indicators for neuroblastoma were also spotted on the array.

Ten micrograms of each total RNA were labeled by using CyScribe™ RNA labeling kit according to a manufacturer's manual (Amersham Pharmacia Biotech), followed by probe purification with Qiagen MinElute™ PCR purification kit (Qiagen). A mixture of an equal amount of RNA from each of four neuroblastoma cell lines (NB69, NBLS, SK-N-AS, and SH-SY5Y) was used as a reference. RNAs extracted from primary neuroblastoma tissues and those of reference mixture were labeled with Cy3 and Cy5 dye, respectively, and used as probe together with yeast tRNA and polyA for suppression. Subsequent hybridization and washing were performed as described previously (Takahashi, M. et al. Cancer Res 62, 2203-9 (2002); Yoshikawa, T. et al. Biochem Biophys Res Commun 275, 532-7 (2000)). The hybridized microarrays were scanned using an Agilent G2505A confocal laser scanner (Agilent Technologies, Inc.) and the fluorescent intensities were quantified by GenePix™ Pro microarray analysis software (Axon Instruments, Inc.).

1-3. Data Preprocessing

To remove the biases of microarray system, the LOWESS normalization (Quackenbush, J. Nat Genet 32, 496-501 (2002)) was used. When the Cy3 or Cy5 strength for a clone was smaller than 3, it is regarded as abnormally small, and the log expression ratio of the corresponding clone is treated as a missing value. The rate of such missing entries was less than 1%. After the normalization of a 5,340 (genes)-by-136 (samples) log expression matrix and missing value removal, each missing entry was imputed to an estimated value (Oba, S. et al. Bioinformatics (2003)).

Normalization is necessary for removing various uninteresting artifacts like unequal cDNA quantities on a slide, efficiency difference between two fluorescence dyes, and others. Several reports have suggested that the log Cy3-Cy5 ratio is significantly dependent on fluorescence intensity of each gene. In order to remove such systematic biases, a locally weighted linear regression (LOWESS) normalization (Cleveland, 1979; Quackenbush, 2002) was used, which removes the intensity-dependent biases. The normalized log expression ratio $y_i$ of gene i is given by $$y_i = \log Cy3_i - \log Cy5_i - f(\log Cy3_i + \log Cy5_i),$$

where $Cy3_i$ and $Cy5_i$ are Cy3 and Cy5 fluorescence strength of gene i, respectively. $f(x)$ is a normalization function, which represents the intensity-ratio (I-R) bias, and is estimated using all spots on a single slide. Normalization across slides was not considered.

For a 5,340-by-136 log expression ratio matrix after the LOWESS normalization and the removal of suspicious log-ratio values, each missing entry was imputed to an estimated value, by the Bayesian PCA imputation method (BPCAfill) proposed by us previously (Oba et al., 2003). By evaluating the BPCAfill prediction for 1% missing values added artificially to the expression matrix, the root mean squared prediction error by BPCAfill was estimated as 0.2, which is consistent with the reproduction standard deviation of duplicated genes, 0.3.

1-4. Supervised Machine Learning and Cross Validation

The 116 samples whose prognosis after 24 months had been checked were used to train a supervised classifier that predicts the prognosis of a new patient. Selecting genes that are related to the classification is an important preprocess for reliable prediction. Therefore, after omitting genes whose standard deviation over the 116 slides was smaller than 0.5, N genes where N is determined by a cross-validation technique were selected, based on the pair-wise correlation method.

If a supervised classifier using all of the 5,340 genes was constructed, the prediction for a new sample is not reliable. This is a typical problem of microarray analyses, in which the number of genes is usually much larger than that of samples. Therefore, selecting genes that are related to the classification (discrimination) is important for reliable prediction.

The inventors first omitted genes whose standard deviation over the 116 slides was smaller than 0.5. After that, the inventors selected N genes based on the following criterion, where the number N is determined by a cross-validation technique. In the fields of statistical pattern recognition, univariate feature extraction based on t statistics, permutation p-value, or so on, has been used for feature extraction. In our case, a univariate feature extraction corresponds to a gene-wise selection ignoring correlation among genes. According to the pair-wise method (Bo, T, & Jonassen, I. Genome Biol 3, (2002)), on the other hand, a pair-wise correlation is considered in the gene selection so that higher discrimination accuracy is obtained using a smaller number of genes. Although t statistics was used in the original work (Bo and Jonassen, 2002), the following pair-wise F score was used in the gene selection.

In a binary discrimination problem between class 1 ($n_1$ samples) and class 2 ($n_2$ samples), using the expression ratio of a single gene, it is required to determine a discrimination threshold. Let $p_1$ and $p_2$ denote the discrimination accuracy for samples in classes 1 and 2, respectively. The F value for this single gene is then given by the harmonic mean of $p_1$ and $p_2$: $F = 2 p_1 p_2/(p_1+p_2)$. When the F value is maximized with respect to the discrimination threshold, it is called the F score of that gene. The F value is more robust than the t statistics especially when outliners exist and/or there is unbalance between $n_1$ and $n_2$. Similarly to an F value of a single gene, the inventors define an F value of a gene pair. Using two genes, i and j, construct a linear discriminator in the two dimensional space composed by expression ratios of genes i and j. By optimizing the linear discriminator in the two dimensional space, an F score for a gene pair (i, j) is obtained. Pair-wise F-value (PF) scores are then calculated by the following procedure.

Calculate F scores for all genes and select into a pool of 500 genes whose individual F scores are the largest. Let PF scores of the not-selected genes be zero.

For every pair of 500 genes in the pool, calculate an F score.

Take out the pair whose F score is the largest from the pool, so that the F scores for the two genes are the same as the F score of that pair.

Until there are no more genes in the pool, repeat step 3.

The inventors used PF scores for selecting N genes in the gene selection.

GP classifiers were used for the supervised classification. Among the 116 samples, 29 test samples were selected so that their prognosis factors have similar distributions to those of the 116 samples. The remaining 87 training samples were further separated into 78 learning samples and 9 validation samples. A supervised GP classifier was trained by the learning samples and assessed by the validation samples. This process was repeated 100 times (see FIG. 1) by varying the learning and training samples and obtained mean discrimination accuracy. Here, the gene selection based on the pair-wise correlation method was executed for each learning data. Thus, the gene selection procedure was also assessed, though this assessment has often been ignored in various microarray studies.

From the analysis to compare two types of kernel functions, a polynomial kernel and a Gaussian kernel, a Gaussian kernel was better, because the number of genes was smaller, the accuracy of the outcome prediction was higher, and more stable against the noise with a Gaussian kernel. The inventors therefore concluded that the Gaussian kernel is better than the polynomial kernel in the outcome prediction of neuroblastoma, and chose the former in this study.

1-5. Clustering Analysis and Survival Analysis

For unsupervised clustering, Gaussian kernel functions were also used. The inventors defined distance measure based on Gaussian kernels obtained through the supervised classification process (see above). Each sample is represented by a feature vector defined by the kernel function, and the distance of two feature vectors was measured as a Pearson's correlation of the vectors. This clustering in the kernel space could exhibit more robust cluster structures than those by the conventional hierarchical clustering.

The Kaplan-Meier survival analysis was also programmed by us and used to compare patient survival. To assess the association of selected gene expression with patient's clinical outcome, the statistical p-value was generated by the log-rank test.

2. Results

2-1. Neuroblastoma-Proper cDNA Microarray and Gene Expression in 136 Primary Tumors The inventors have so far obtained 5,500 genes from the mixture of oligo-capping cDNA libraries generated from 3 primary neuroblastomas with favorable outcome (stage 1, high TrkA expression and a single copy of MYCN), 3 tumors with poor prognosis (stage 3 or 4, low expression of TrkA and amplification of MYCN), and a stage 4s tumor Oust before starting rapid regression) (Ohira et al., 2003a, 2003b: non-patent documents 19 and 20). The inventors then made a neuroblastoma-proper cDNA microarray harboring the spots of 5,340 genes onto a slide glass using a ceramics-based ink-jet printing system. This in-house cDNA microarray appeared to have overcome the previous problems caused by pin-spotting such as an uneven quantity or shape of the individual spots on an array. Ten μg each of total RNA extracted from the 136 frozen tissues of primary neuroblastomas was labeled with Cy3 dye. As a common reference, the mixture of total RNA obtained from 4 neuroblastoma cell lines with a single copy of MYCN (NB69, NBLS, SK-N-AS, and SH-SY5Y) was labeled with Cy5 dye. The inventors have randomly selected the tumor samples from the neuroblastoma tissue bank and hybridization was successfully performed in 136 tumors consisting of 41 in stage 1, 21 in stage 2, 34 in stage 3, 28 in stage 4, and 12 in stage 4s. The stage 4s neuroblastoma shows special pattern of clinical behavior and its widespread metastases to skin, liver and bone marrow regress spontaneously. Sixty-eight tumors were found by mass screening of the urinary cathecolamine metabolites at 6 months after birth. The follow-up duration was ranged from 3 to 239 months (median: 32 months, mean: 50.6 months) after diagnosis (see FIG. 3).

Figure 10:
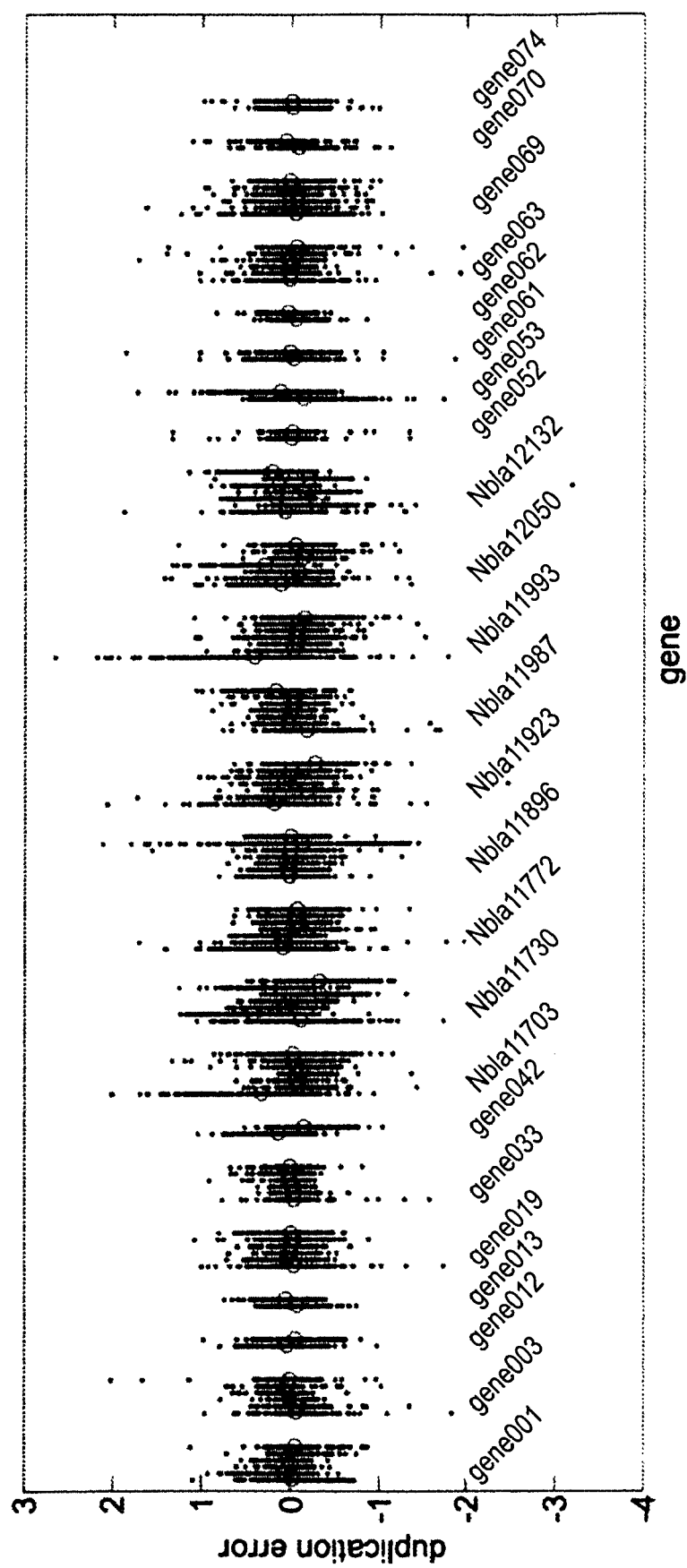
FIG. 10 shows chip quality and reproducibility. Deviation of the normalized log expression ratio from its average. For each gene spot, blue dots, a red circle, and a pair of green dots denote log expression ratio for the 136 samples, the average over the samples, and the standard deviation (upper and lower) over the samples, respectively. The horizontal axis denotes a gene identifier, and duplicated spots have the same identifier. If red circles do not much vary within the spots labeled by a single identifier, the log expression ratio of that gene has high reproducibility.

The inventors first evaluated the quality of our cDNA microarray. The log Cy3/Cy5 fluorescence ratio of each gene spot was normalized to eliminate the intensity-dependent biases. Since our cDNA microarray contains 260 duplicated or multiplicated genes, the expression ratio of such a duplicated gene was represented by the average of the multiple spots. Based on the estimation performance for missing values (see Supplemental data, below) and the reproduction variance of duplicated genes, the standard deviation of log-ratio of a single gene was about 0.2-0.3, which was sufficiently small (FIG. 10). The scattered plots of log Cy3/Cy5 fluorescence ratio between the duplicated gene spots in 136 experiments and those between repeated experiments also indicated the reproducibility of spotting and experiment (Suppl. FIG. S1B and S1C). These suggest that our cDNA microarray was highly quantitative and reproducible.

2-2. Supervised Classification

To develop a statistical tool that predicts the prognosis of a new patient with the tumor, the inventors introduced a supervised classification. Since the variation of follow-up duration created the noise in the supervised classification, the inventors used the patient's outcome (dead or alive) at 24 months after diagnosis as the target label to be predicted. Because the outcome of 20 of 136 samples are unknown at 24 months after diagnosis, the rest 116 sample data were used subsequently (FIG. 1). The inventors first omitted the genes whose standard deviation over the 116 slides was smaller than 0.5, because the background noise level was about 0.3 (see above). The inventors then selected N genes based on the following criterion, where the number N is determined by a cross-validation technique. Gene selection was performed according to a variation of the pair-wise correlation method (Bo and Jonassen, 2002) to obtain a higher discrimination accuracy using a smaller number of genes (see FIG. 13).

The inventors decided to use Gaussian-kernel Gaussian Process (GP) classifiers for the supervised classification. A GP classifier is one of kernel-based classifiers (MacKay. D. J. C. Neural Network and Machine Learning, 133-165 (1998)). It resembles support vector machine (SVM) classifiers, but is based on a probabilistic model and has an advantage when interpreting the output.

2-3. Test and Cross Validation

The 116 samples were in advance separated into 87 training samples used for calculating the supervised classifier and 29 test samples to evaluate the obtained classifier (FIG. 1). In the training phase, the inventors never used the 29 test samples. The training samples were further separated into learning samples (~90%) and validation samples (~10%), and both of the gene selection and the parameter determination were assessed by a cross-validation technique.

Figure 2:
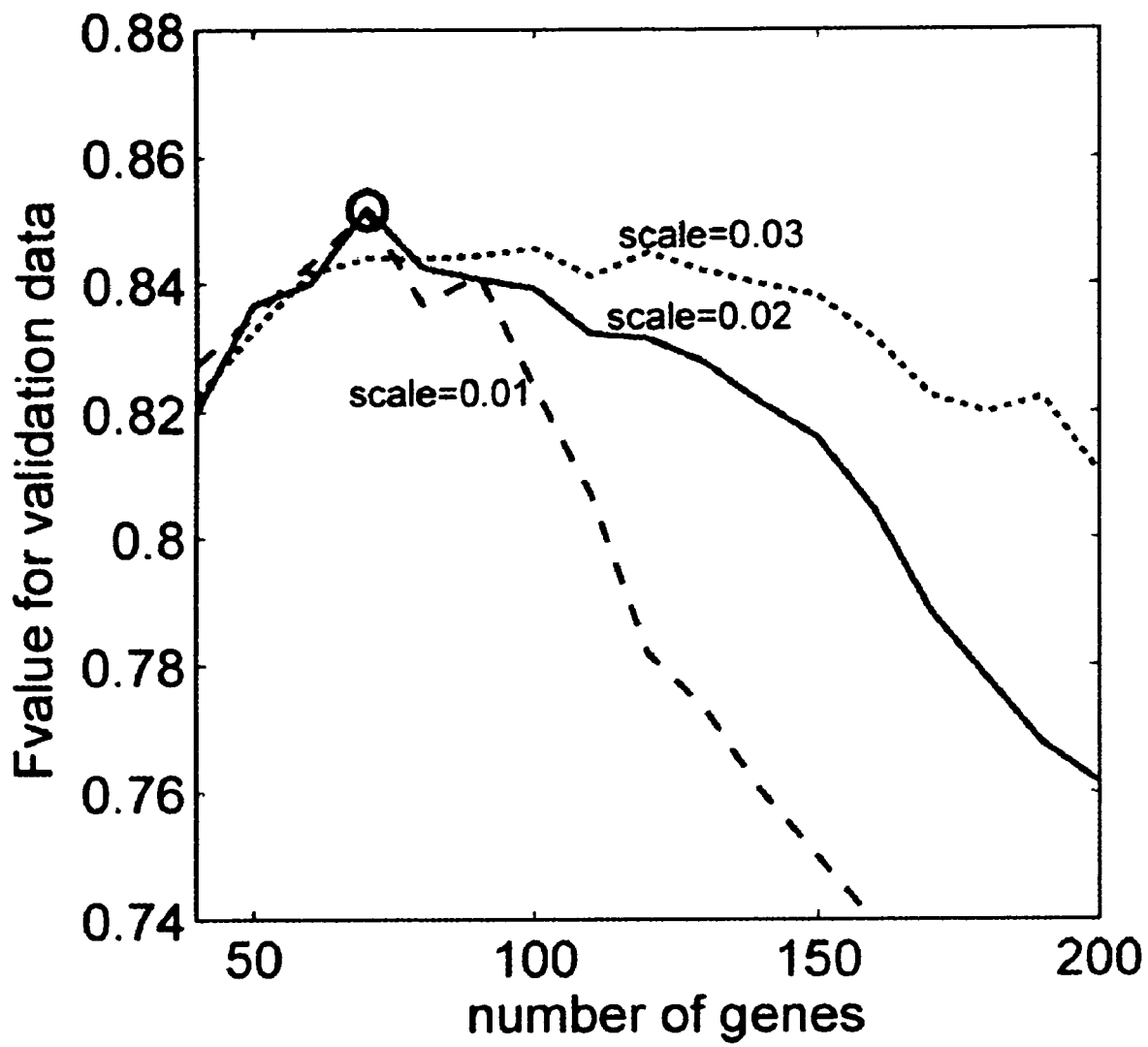
FIG. 2 shows discrimination accuracy (F-value) by the Gaussian-kernel GP classifier for various numbers of genes, N. Different line type indicates a different parameter value (scale parameter used in the Gaussian kernel). Blue circle denotes the best accuracy at scale=0.02. (N=70)

A GP classifier outputs a posteriori probability (posterior) of each sample, which represents the predictive probability that the patient's prognosis is poor. An accuracy represents the rate of correct prediction, when binary prognosis prediction is done based on whether the posterior is larger than a threshold 0.5. F-value is the harmonic mean of accuracy over favorable and unfavorable neuroblastoma samples (see FIG. 13). FIG. 2 shows the F-value by the Gaussian-kernel GP classifier, for various numbers of genes, N. The best number of genes was thus determined as N=70 by the cross-validation technique.

Figure 3A:
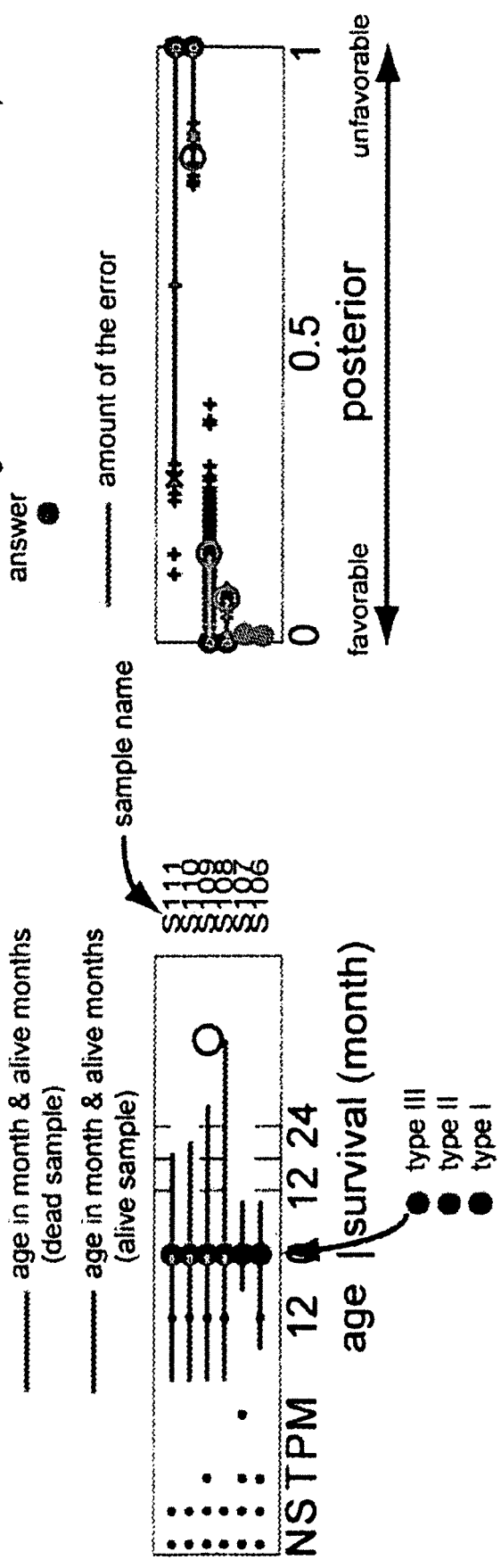
FIG. 3 is posterior probability of unfavorable prognosis after 24 months for 87 learning data samples, output by the Gaussian-kernel GP classifier. Left panel: Neuroblastoma samples. Right panel: Prediction by a GP classifier with a Gaussian kernel of scale 0.02 and N=70. A green circle denotes an answer; if it is located to the rightmost (leftmost) position, the answer for that sample is 'dead' ('alive'). A '+' mark denotes the posterior value predicted by the GP classifier, in a case that the sample belonged to a validation data set among 100 cross-validation trials, and a red circle or cross denotes the mean over such validation trials. The red line is the difference between the answer and the mean (red circle or cross); the longer, the worse the prediction of the classifier is.
Figure 3B:
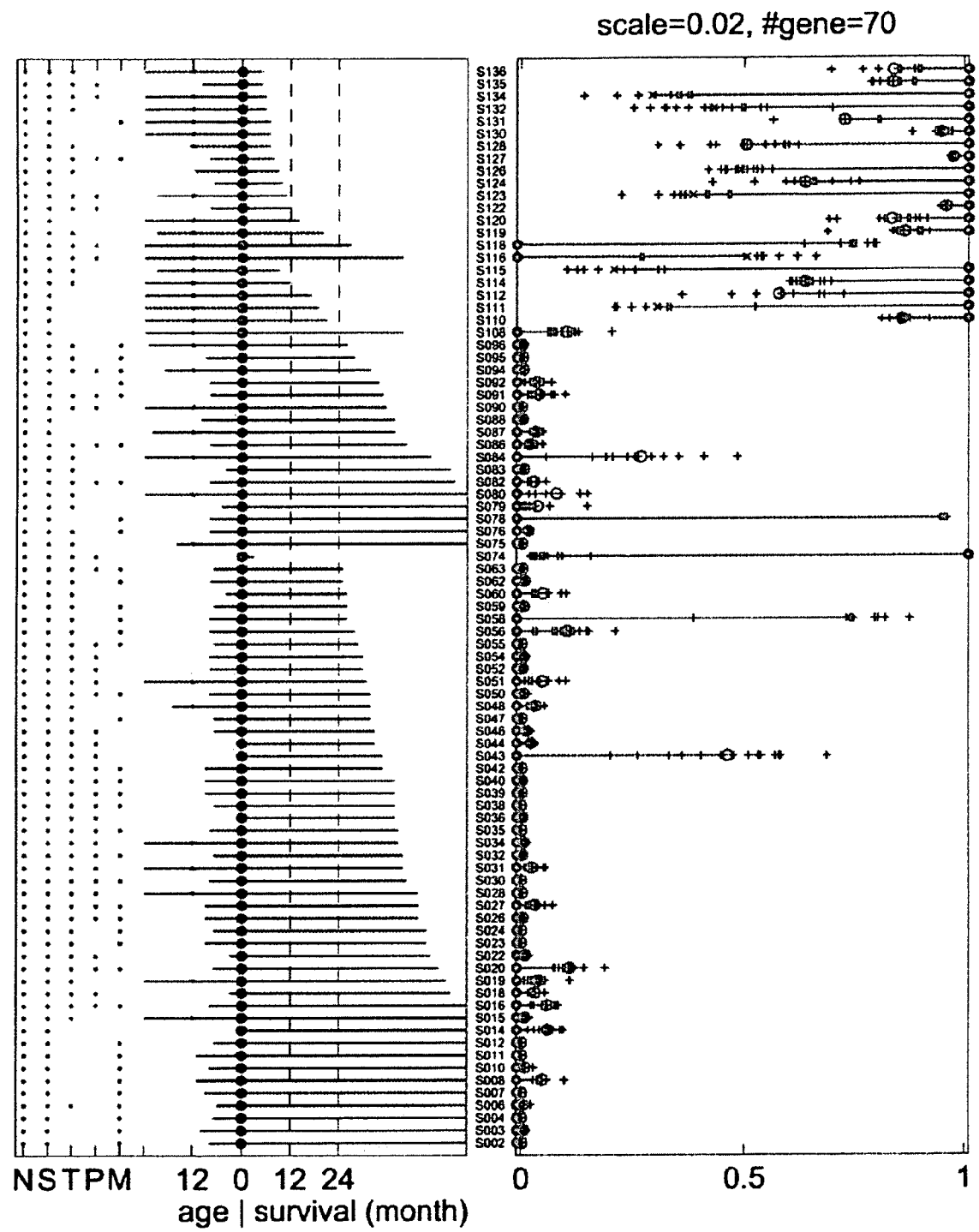
Figure 4:
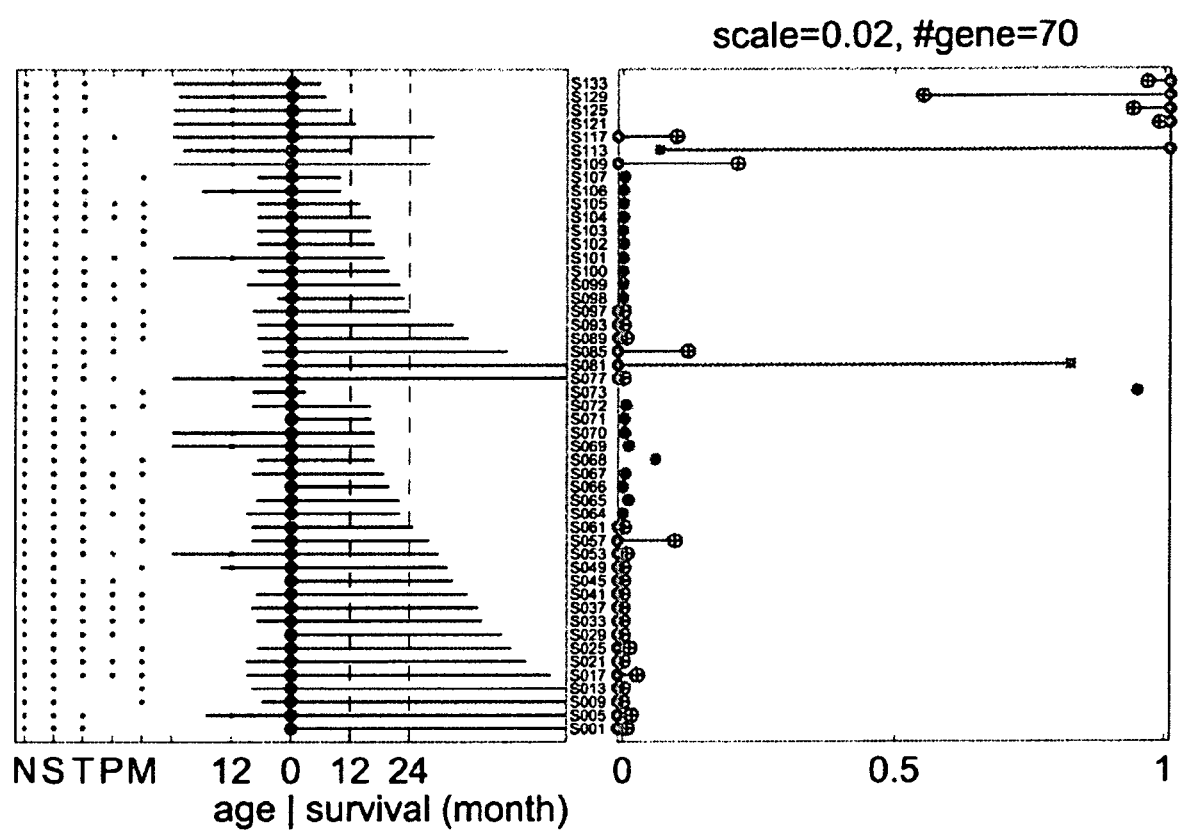
FIG. 4 is posterior probability of unfavorable prognosis after 24 months, output by the Gaussian-kernel GP classifier. 29 new samples were used for test and additive 20 samples are also shown whose prognosis at 24 months is unknown. Other information is same as those of FIG. 3.

FIG. 3 shows the posterior of the 87 training samples by the GP classifier whose parameter was optimally tuned by the cross-validation. Accuracy for the training samples, which was evaluated by the cross-validation, was 87% (76/87). FIG. 4 shows the results when the prognosis of the 29 test samples was predicted by the GP classifier. F-value and accuracy were 0.80 and 93%, respectively. Except for S113 (posterior: 0.32; stage 4, 22-month-old, single copy of MYCN, low TrkA, dead 12 months after diagnosis) and S081 (posterior: 0.86; stage 3, 6-month-old, single copy of MYCN, low TrkA, alive 62 months after diagnosis), the prognosis for all the test samples was correctly predicted (27/29, 93%).

Figure 5:
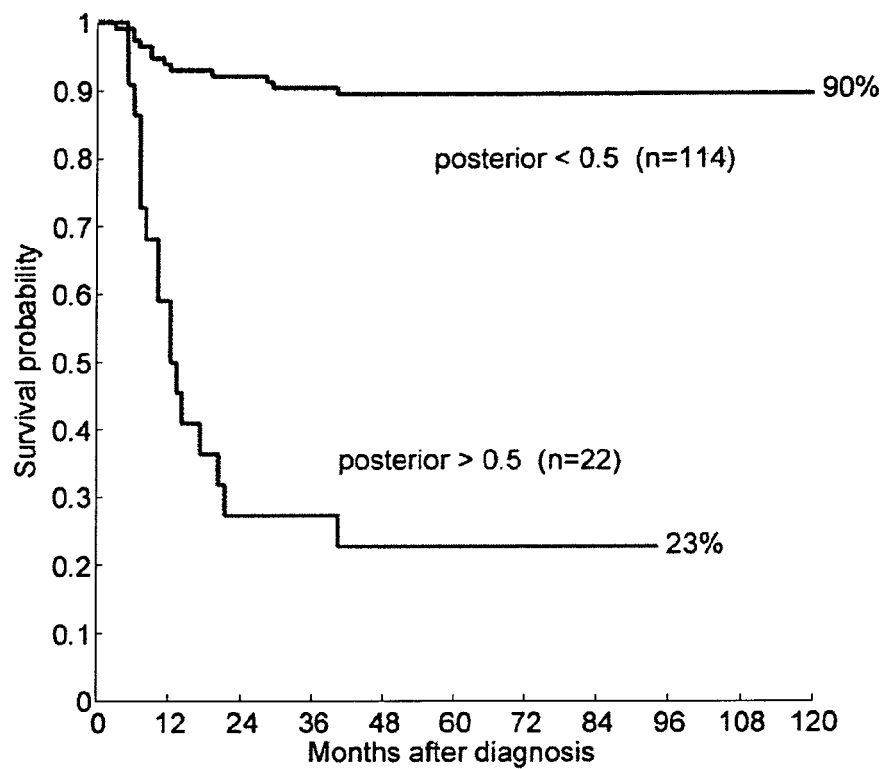
FIG. 5 is disease-free survival of patients stratified based on the posterior value. Kaplan-Meier's survival curves for neuroblastoma samples with posterior>0.5 (red) and those with posterior<0.5 (blue). The posterior was obtained by a leave-one-out analysis with the Gaussian-kernel GP classifier. P-value of log-rank test between red and blue lines was much smaller than $10^{-5}$.
Figure 6:
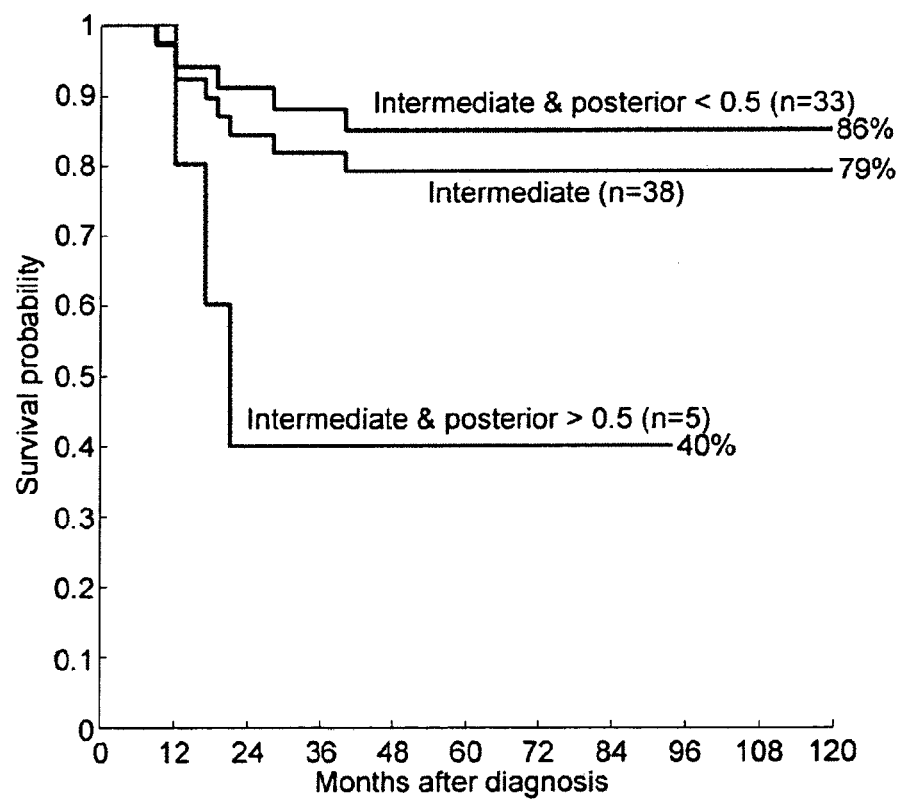
FIG. 6 is disease-free survival of patients stratified based on the posterior value, as same as FIG. 5. Kaplan-Meier's survival curves for neuroblastoma samples in the intermediate subset (Type III) with posterior>0.5 (red), posterior<0.5 (blue) and together (green). P-value of log-rank test between red and blue was much smaller than $10^{-5}$.

FIG. 5 shows survival curves for the patients with posterior<0.5 (favorable) and posterior>0.5 (unfavorable) according to the GP classifier. The 5-year survival rate of the former is 90%, whereas that of the latter 23% $p<10^{-5}$). To further evaluate the efficiency of our system, the posterior value was calculated for the intermediate subset of neuroblastoma (stage 3 or 4, without amplification of MYCA) whose prognosis is usually difficult to be predicted. As shown in FIG. 4B, the survival curves were significantly segregated into two groups. The 5-year survival rate of the patients with posterior<0.5 was 86%, while that of the patients with posterior>0.5 was 40% p<10-5). These results suggest that the posterior value obtained by our supervised classifier is able to classify the outcome of neuroblastomas with high efficiency, even of the intermediate type of the tumors.

1-4. Leave-One-Out Analysis

Figure 7:
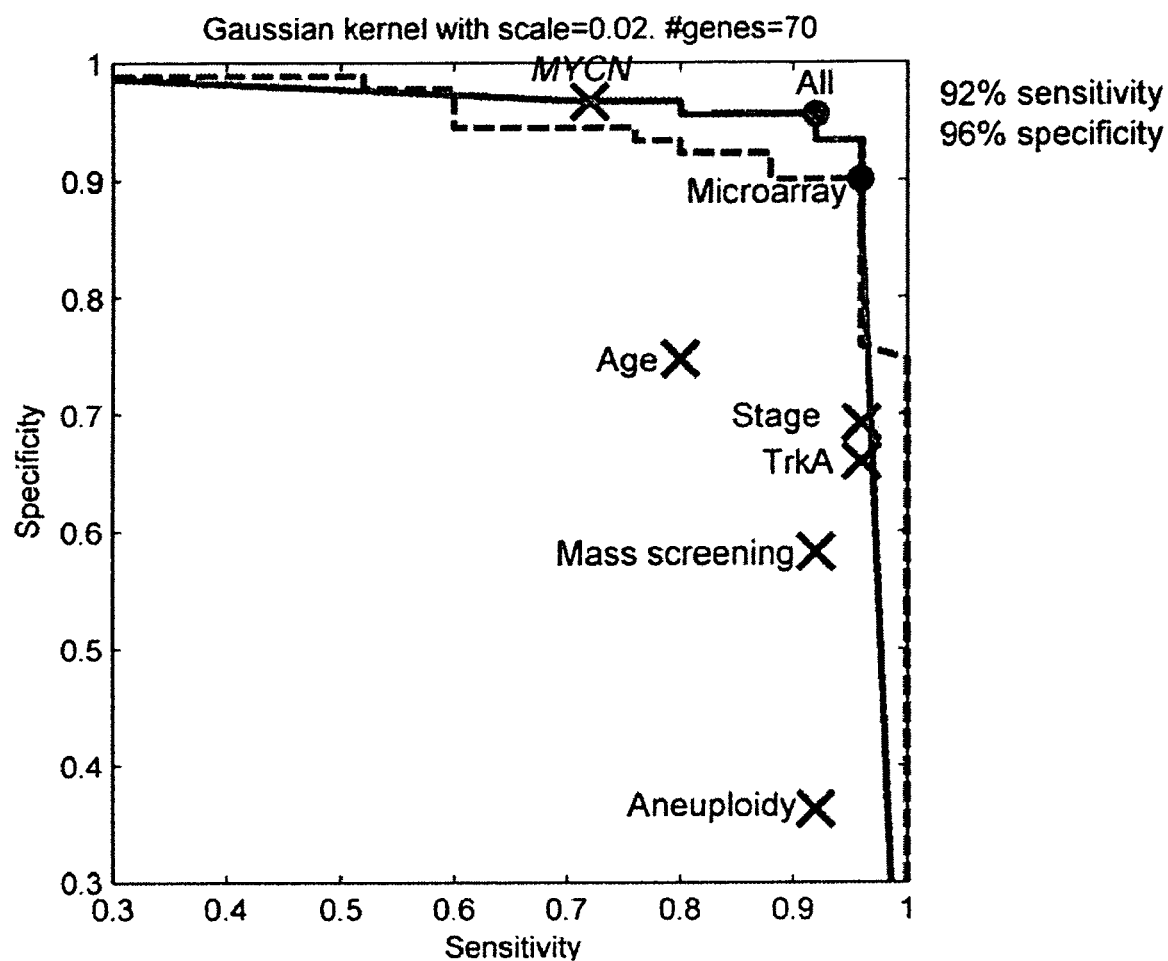
FIG. 7 shows receiver operating characteristic (ROC) curves. Performance of prognosis markers and the Gaussian-kernel GP classifier in the two-dimensional plane of sensitivity and specificity is shown. Sensitivity (horizontal axis) is the rate of correct prediction among favorable samples, and specificity (vertical axis) is the rate of correct prediction among unfavorable samples. Since the upper-right corner represents 100% sensitivity and 100% specificity, a classifier located at that position is ideal. A blue cross 'x' denotes a sensitivity-specificity point achieved by prognosis marker. A blue circle 'o' denotes the prediction by the combination of three existing markers, 'Age', 'Stage' and 'MYCN'. A GP classifier outputs its prediction as posterior, a real value. Since its binary prediction, favorable or unfavorable, depends on the threshold, a curve on the sensitivity-specificity plane can be plotted by changing the threshold. Such a curve is called a receiver operating characteristic (ROC) curve. A magenta broken line denotes prediction using only microarray data, a green broken line denotes prediction using microarray data and the 'Stage' marker, and a red real line denotes prediction using microarray data, and 'Age', 'MYCN' and 'Stage' markers.

To evaluate how useful the posterior value is for predicting the prognosis as compared with the other conventional markers, the inventors introduced the leave-one-out cross-validation method to the predicted prognosis of all 116 patients. FIG. 7 shows the receiver operating characteristics (ROC) curve which indicates performance of each or combination of the GP classifier and the other clinical as well as molecular prognostic factors (age, stage, TrkA expression, MYCN amplification, DNA ploidy, and the tumors found by mass screening) in the two-dimensional plane of sensitivity (the rate of correct prediction among alive samples) and specificity (the rate of correct prediction among dead samples). The markers are good to predict the outcome at either high sensitivity or high specificity. In good accordance with the previous reports, age (less than one-year-old), stages (1, 2 and 4s), high TrkA expression, hyperdiploidy (aneuploidy), and the tumors found by mass screening showed high sensitivities of 80%, 97%, 97%, 92%, and 93%, respectively, whereas their specificities were 76%, 69%, 66%, 37%, and 58%, respectively. On the other hand, MYCN amplification showed 72% sensitivity and 97% specificity. In comparison to these conventional markers, prediction by the GP classifier exhibited good balance between sensitivity (96%) and specificity (90%), and totally it is superior to the other markers. Moreover, the combination of supervised classification and three typical prognostic markers (age, stage and MYCN amplification) has achieved as much as 92% sensitivity and 96% specificity.

1-5. Clustering Analysis

Figure 8:
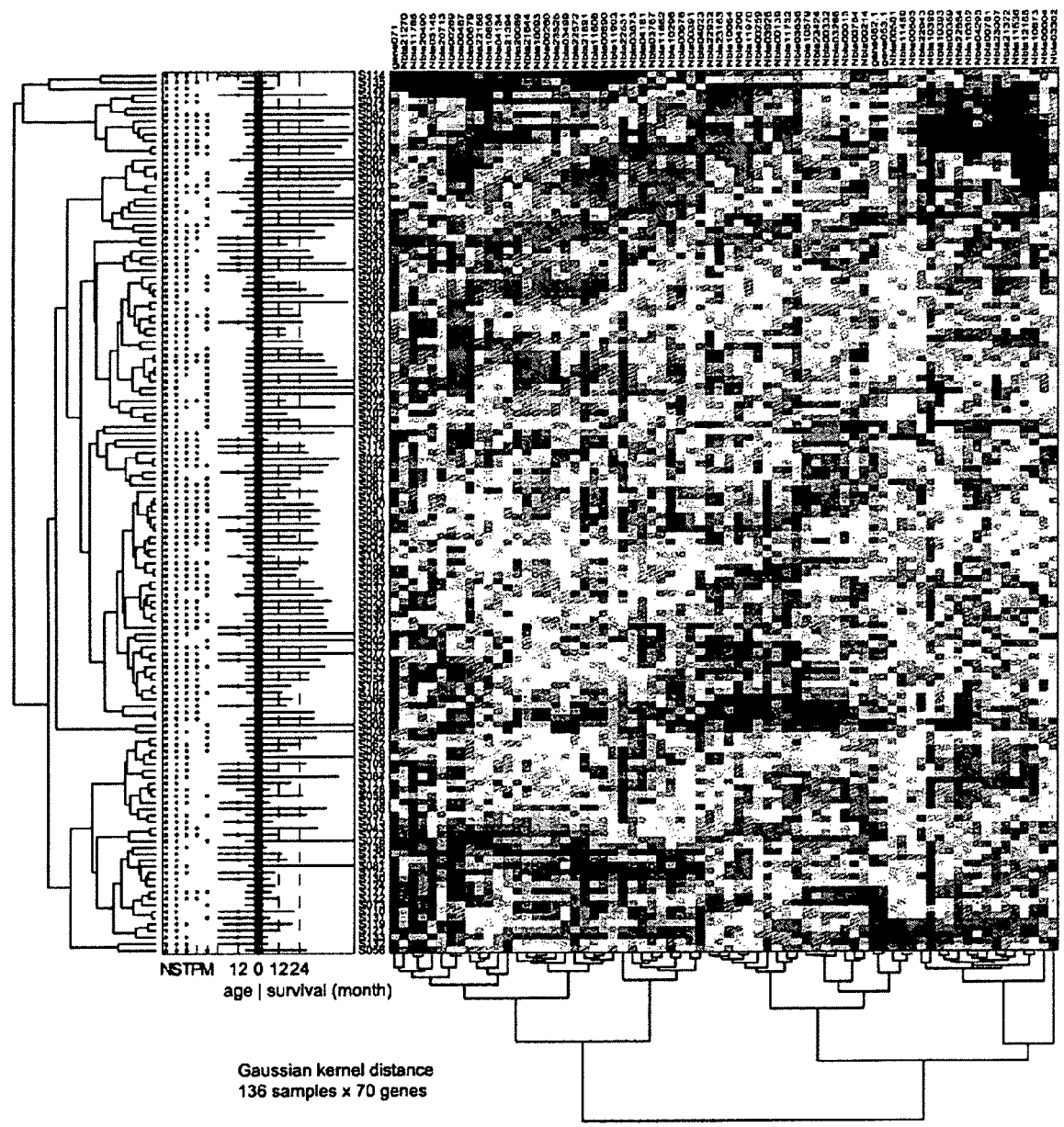
FIG. 8 shows expression profiles of the 70 genes selected for predicting the prognosis. Unsupervised clustering of 136 neuroblastoma samples and the 70 genes selected in this study, based on the Gaussian kernel. Blue; type I tumor, Green; type II tumor, Red; type III tumor (see text). The expression of each gene in each sample is represented by the number of standard deviations above (red) or below (blue) the mean for that gene across all 136 samples.
Figure 9:
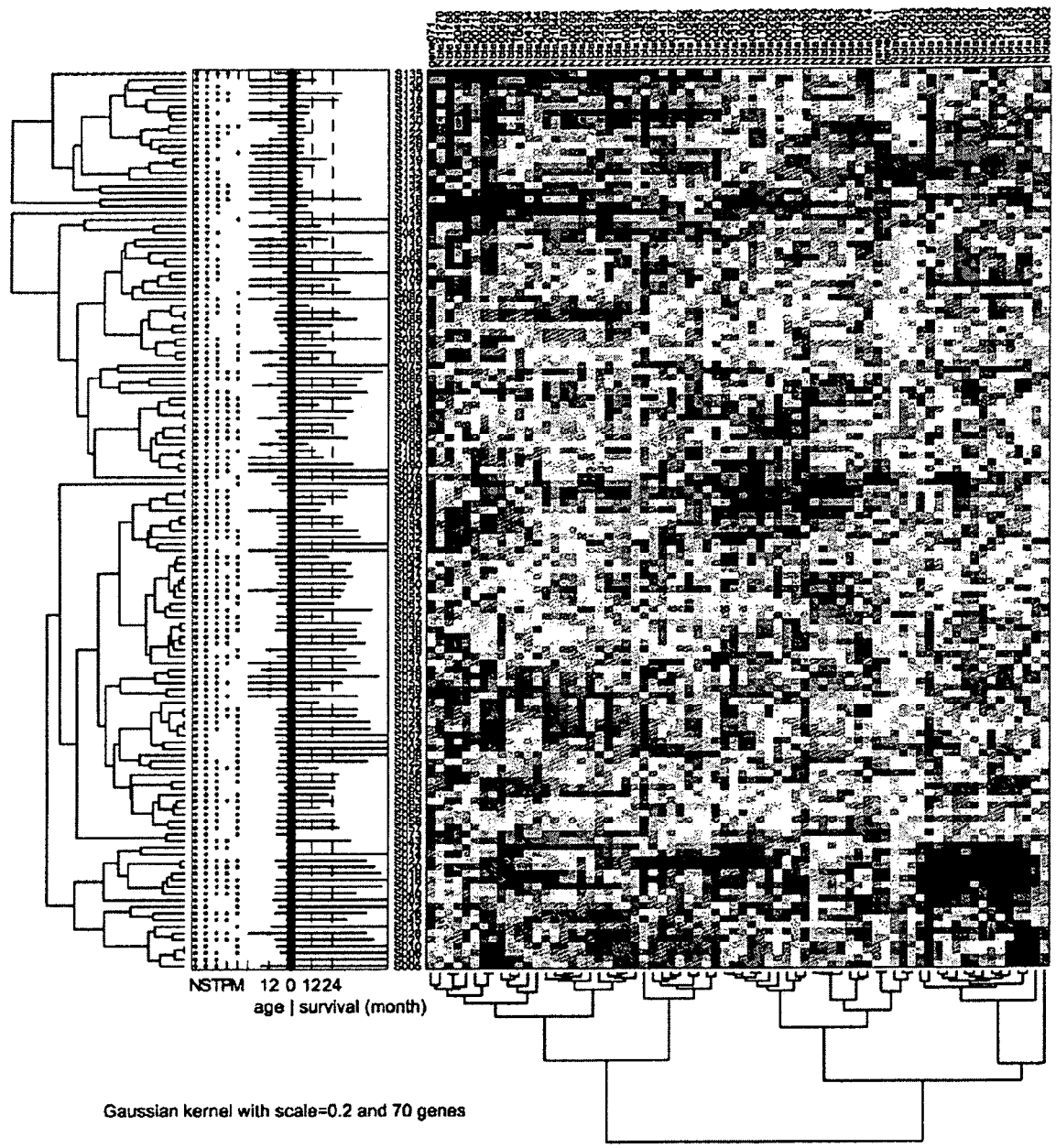
FIG. 9 is clustering of the samples within the three tumor groups according to the 70 genes' expression shown in FIG. 9.

To assess the relationship between the clinically defined subsets of neuroblastoma and expression of the 70 genes selected as top-scored based on the pair-wise correlation method, the inventors performed an unsupervised clustering analysis in the kernel space (FIGS. 8 and 9). For better understanding of the results, the inventors introduced Brodeur's classification of neuroblastoma subsets: type I (stages 1, 2 or 4s, a single copy of MYCN; blue marks in FIGS. 3, 4, 8 and 9), type II (stage 3 or 4, a single copy of MYCN; green marks in FIGS. 3, 4, 8 and 9), and type III (all stages, amplification of MYCN; red marks in FIGS. 3, 4, 8 and 9) (Brodeur et al., 199?). FIG. 8 shows that many of the type III tumors were clustered in a group with highly expressed genes in about a half of 70 (gene group UF, as the gene group strongly correlated with unfavorable prognosis, see below) and lowly expressed genes in the rest half (gene group F, as the gene group strongly correlated with favorable prognosis, see below). On the other hand, type I tumors formed a broad expression pattern with heterogeneous gene clusters. Interestingly, type II tumors were not uniformly clustered but distributed among the types I and III tumors. To further understand from the clinical point of view, the unsupervised clustering was reorganized according to each type (FIG. 9). Intriguingly, a part of the type II tumors of the patients with poor prognosis showed a similar expression pattern to that of the type III and many of them were dead. On the other hand, expression profiles of the rest of the type II tumors seemed to be heterogeneous similarly to those of the type I tumors with favorable outcome. Most of the tumors with high expression of TrkA and hyperdiploidy as well as the mass screening tumors were included in the latter group. Thus, the tumors in the type II intermediate group were roughly segregated into two subgroups with favorable and unfavorable prognosis. The fact that the clustering pattern in FIGS. 8 and 9 is rather complex may also support the fact that our prognostic prediction is based on the decision by majority of the selected genes.

Table 2 shows the list of the 70 top-scored genes and their p-values of the log-rank test. The gene with the highest score was tubulin alpha (TUBA1). Based on the above clustering, the 70 genes were segregated into two groups (group F and group UF) (FIGS. 8 and 9, and Table 2). The genes in group F had a tendency to show high levels of expression in the type I tumors, whereas those in group UF were expressed at high levels in the type III tumors. The differential expression of those genes between the subsets of neuroblastoma was further confirmed by semi-quantitative RT-PCR (a part of the results were reported in Ohira et al., 2003a: non-patent document 19). The genes in group F contained those related to neuronal differentiation [tubulin alpha, peripherin, HMP19, and neuromodulin (GAP43), etc.] and those related to catecholamine metabolism [tyrosine hydroxylase (TH) and dopa decarboxylase (DDC)]. On the other hand, the genes in group UF involved many members of the genes related to protein synthesis (ribosomal protein genes, elongation factor genes EEF1A, G, and EIF3S5, etc.) and those related to metabolism [nucleophosmin, enolase 1 (ENO1), and transketolase (TKT), etc.]. MYCN gene was also a member of group UF as expected. The very high levels of expression of MYCN and DDX-1, both of which are frequently co-amplified, were found in the type III tumors with poor prognosis. The p-values of the log-rank test in 24 out of 33 genes in group F and those in 30 of 37 genes in group UF were less than 0.05, indicating that all of the 54 genes with a significant p-value can be the independent prognostic factors of primary neuroblastomas.

TABLE 2

The 70 genes selected by the Gaussian-kernel GP classifier

| | Gene Code | Gene Name | Accession No. | Definition | log rank P-value |
|---|---|---|---|---|---|
| Group F | gene071 | TH | NM_000360 | tyrosine hydroxylase | <0.001 |
| | Nbla21270 | AK095244 | AK095244 | EST | <0.001 |
| | Nbla11788 | PRPH | NM_006262 | peripherin | 0.022 |
| | Nbla20490 | PHPH? | NM_006262 | 5'upstream region of peripherin | 0.004 |
| | Nbla03145 | ECEL1 | NM_004826 | endothelin convening enzyme like 1 | 0.227 |
| | Nbla20713 | HAND2 | NM_021973 | basic helix-loop-helix transcription factor HAND2 | 0.473 |
| | Nbla00269 | DBH | NM_000787 | dopamine beta-hydroxylase type a (EC 1.14.17.1). | 0.935 |
| | Nbla00487 | FLJ13158 | NM_024909 | EST | 0.603 |
| | Nbla00579 | VAT1 | NM_006373 | synaptic vesicle membrane protein VAT1 | 0.924 |

TABLE 2-continued

The 70 genes selected by the Gaussian-kernel GP classifier

| | Gene Code | Gene Name | Accession No. | Definition | log rank P-value |
|---|---|---|---|---|---|
| | Nbla22156 | CLSTN1 | NM_014944 | calsyntenin 1 | 0.814 |
| | Nbla10856 | U5-100K | NM_004818 | U5 snRNP 100 kD protein | 0.665 |
| | Nbla04134 | MBC2 | NM_015292 | membrane bound C2 domain containing protein | 0.439 |
| | Nbla21394 | CHRNA3 | NM_000743 | neuronal acetylcholine receptor protein alpha-3 | 0.066 |
| | Nbla20089 | SEC23B | NM_032986 | protein transport protein SEC236 | 0.003 |
| | Nbla21844 | LOC92906 | NM_138394 | EST | <0.001 |
| | Nbla10093 | HADHB | NM_000183 | mitochondrial 3-ketoacyl-CoA thiolase beta-subunit of trifunctional protein | <0.001 |
| | Nbla00260 | TUBA1 | NM_006000 | tubulin alpha-1 | <0.001 |
| | Nbla23526 | MORF4L2 | NM_012286 | mortality factor 4 like 2 | <0.001 |
| | Nbla03499 | GNB1 | NM_002074 | guanine nucleotide binding protein beta 1 | 0.027 |
| | Nbla22572 | DDC | NM_000790 | dopa decarboxylase | 0.002 |
| | Nbla21891 | VPS41 | NM_014396 | vacuolar protein zoning 41 | <0.001 |
| | Nbla11606 | TUBA3 | NM_006009 | tubulin alpha 3 | <0.001 |
| | Nbla00890 | ARHGEF7 | NM_145735 | Rho guanine nucleotide exchange factor 7 | <0.001 |
| | Nbla11993 | HMP19 | NM_015980 | neuron specific protein family member 2 | <0.001 |
| | Nbla22531 | GAP43 | NM_002045 | neuronal growth associated protein 43 | <0.001 |
| | Nbla03873 | RTN3 | NM_006054 | reticulon 3, neuroendocrine-specific protein | <0.001 |
| | Nbla04181 | AK055112 | NM_032010 | EST | <0.001 |
| | Nbla03767 | MGC8721 | NM_016127 | EST | <0.001 |
| | Nbla11662 | YWHAE | NM_006761 | 14-3-8 epsilon | <0.001 |
| | Nbla10296 | DCTN2 | NM_006400 | dynactin complex 50 kD subunit | <0.001 |
| | Nbla00578 | AF1O | NM_006818 | ALL 1-fused gene from chromosome 1q | 0.002 |
| | Nbla00391 | AF036613 | AF036613 | general transcription factor 2-4 | <0.001 |
| | Nbla04023 | RGS5 | NM_003617 | regulator of G-protein signaling 5 | 0.020 |
| Group UF | Nbla11890 | EEF1A1 | NM_001402 | eukaryotic translation elongation factor 1 alpha | 0.634 |
| | Nbla23163 | EIF3S5 | NM_003754 | eukaryotic translation initiation factor 3, subunit 5 | 0.015 |
| | Nbla10054 | NPM1 | NM_002520 | nucleophosmin | 0.079 |
| | Nbla04200 | RPL4 | NM_000968 | ribosomal protein L4 | 0.196 |
| | Nbla11970 | HNRPA1 | NM_031157 | heterogeneous nuclear ribonucleoprotein A1 | 0.038 |
| | Nbla00259 | RPS6 | NM_001010 | ribosomal protein S6 | 0.168 |
| | Nbla03925 | LAMR1 | NM_002295 | laminin receptor 1 | 0.266 |
| | Nbla00139 | RPS13 | NM_001017 | ribosomal protein S13 | 0.002 |
| | Nbla11732 | RPL5 | NM_002948 | ribosomal protein L5 | 0.016 |
| | Nbla03836 | RPL7A | NM_000972 | ribosomal protein L7a | 0.444 |
| | Nbla10579 | AF432211 | NM_014635 | KIAA0335 | <0.001 |
| | Nbla23424 | no hit | no hit | no hit | <0.001 |
| | Nbla00332 | EEF1G | NM_001404 | eukaryotic translation elongation factor 1 | <0.001 |
| | Nbla03285 | GK001 | NM_020198 | GK001 protein | <0.001 |
| | Nbla00013 | GNB2L1 | NM_006098 | guanine nucleotide binding protein, receptor of activated protein kinase C 1 | <0.001 |
| | Nbla00754 | RPLP1 | NM_001003 | ribosomal protein P1 | <0.001 |
| | Nbla00214 | RPL18A | NM_000980 | ribosomal protein L18a | <0.001 |
| | gene052 | MYCN | NM_005378 | N-myc proto-oncogene protein. | <0.001 |
| | gene053 | MYCN | NM_005378 | N-myc proto-oncogene protein. | <0.001 |
| | Nbla00501 | no hit | NM_000969 | ribosomal protein L5? | <0.001 |
| | Nbla11459 | DDX1 | NM_004939 | DEAD/H (Asp-Glu-Ala-Asp/His) box polypeptide 1 | <0.001 |
| | Nbla00503 | PRSS15 | NM_004793 | protease, serine, 15 | <0.001 |
| | Nbla22643 | FLJ20190 | NM_017705 | hypothetical protein FLJ20190 | <0.001 |
| | Nbla10395 | PCOLCE | NM_002593 | procollagen C-endopeptidase enhancer | <0.001 |
| | Nbla10393 | SHMT2 | NM_005412 | serine hydroxymethyltransferase 2 | <0.001 |
| | Nbla00359 | MAD1L1 | NM_003550 | MAD1 mitotic arrest deficient-like 1 | <0.001 |
| | Nbla22554 | AHCY | NM_006621 | S-adenosylhomocysteine hydrolase-like 1 | <0.001 |
| | Nbla10302 | ENO1 | NM_001428 | enolase 1, (alpha) | <0.001 |
| | Nbla04283 | PKM2 | NM_002654 | pyruvate kinase, M1 isozyme | <0.001 |
| | Nbla00781 | TKT | NM_001064 | uansketolase | <0.001 |
| | Nbla23007 | FKBP10 | NM_021939 | FK506 binding protein 10 | <0.001 |
| | Nbla21322 | GPI | NM_000175 | glucose phosphate isomerase | <0.001 |
| | Nbla11536 | SLC3A2 | NM_002394 | solute carrier family 3 member 2 | <0.001 |
| | Nbla12165 | BSG | NM_001728 | basigin long isoform | <0.001 |
| | Nbla10673 | TRIM28 | NM_005762 | tripartite motif-containing 28 protein | <0.001 |
| | Nbla00004 | RNU2 | BC003629 | small nuclear RNA U2 | 0.003 |
| | Nbla03362 | no hit | no hit | no hit | 0.277 |

3. Discussion

The experimental study demonstrates that the microarray classifier has the best balance between sensitivity (96%) and specificity (90%) among the prognostic factors for predicting the outcome of neuroblastoma. In addition, when it is combined with age at diagnosis, disease stage and MYCN amplification, all of which are currently used as diagnostic tools at the bedside, the specificity can be increased up to 96%. Furthermore, the intermediate subset of neuroblastomas (type II), which are usually difficult to predict the long term outcome, have also been segregated by the microarray into the groups with favorable and unfavorable prognosis.

Figure 11:
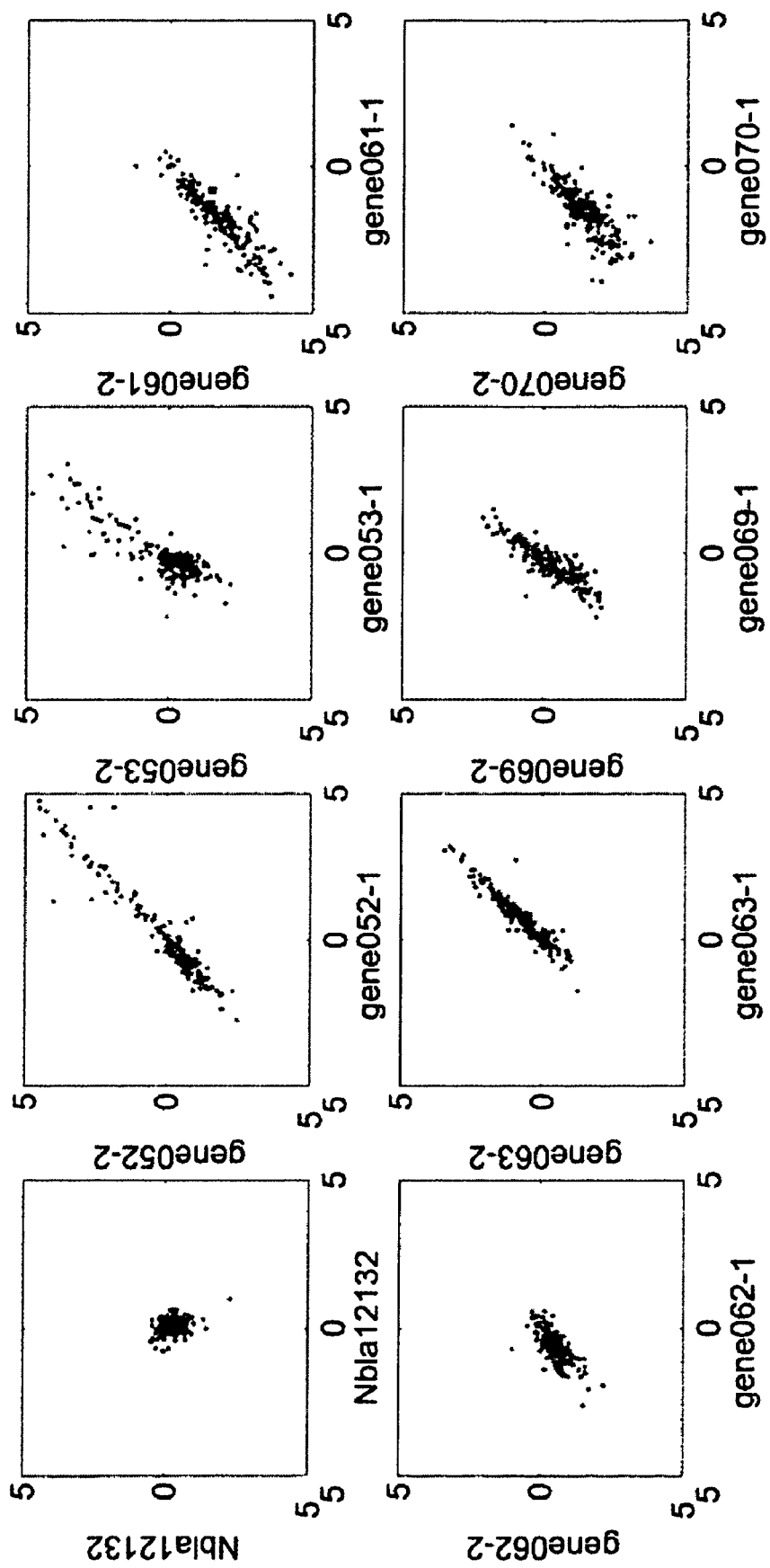
FIG. 11 also shows chip quality and reproducibility. Scatter plots for eight pairs of duplicated spots in a slide, where each dot denotes the expression of two spots of the same gene in a single slide. Horizontal and vertical axis denote $\log_2$ expression ratios. Root mean squared variance of each pair is about 0.2.
Figure 12:
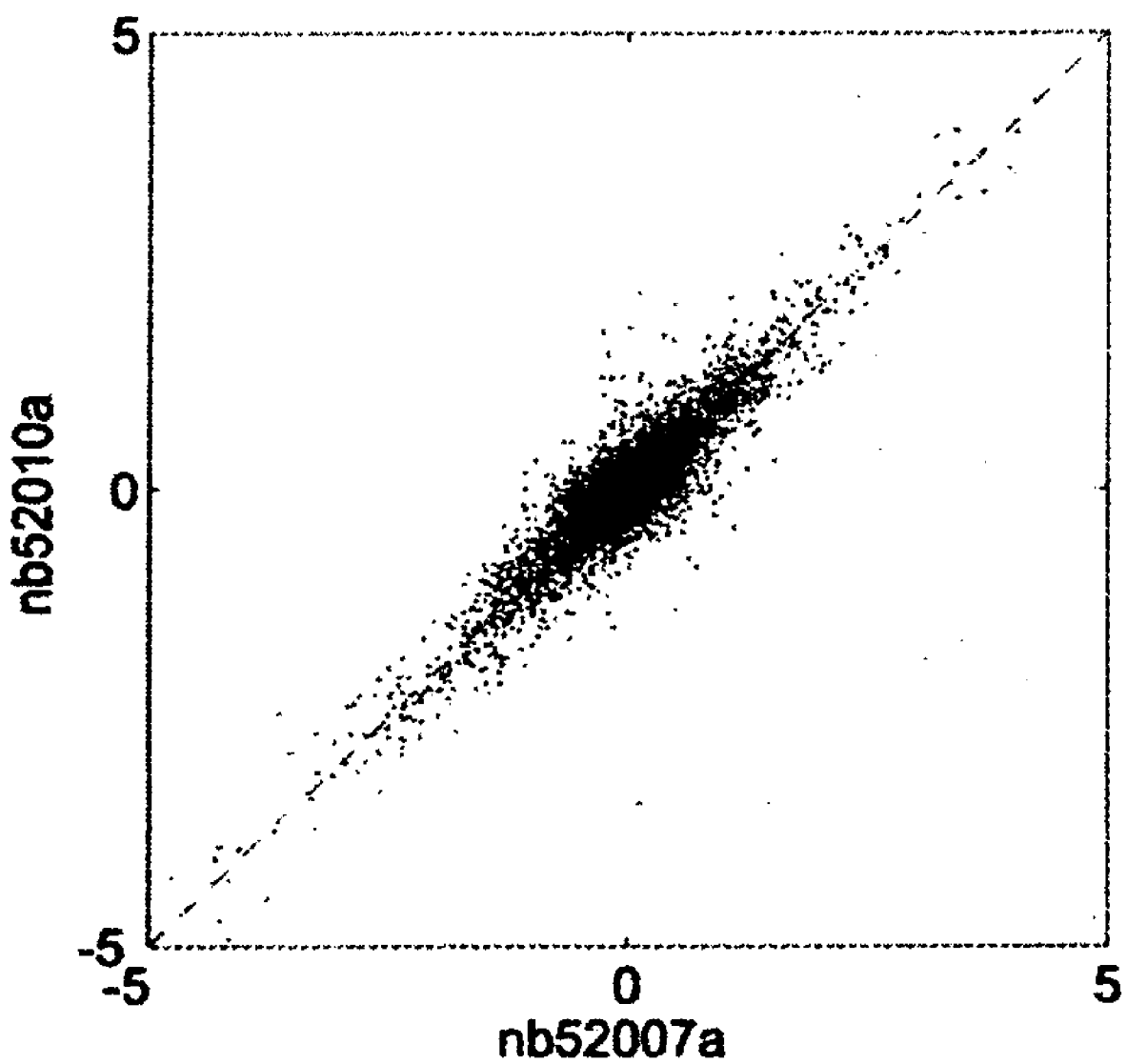
FIG. 12 further shows chip quality and reproducibility. Reproducibility of the same spot between two different slides. Horizontal and vertical axis denote $\log_2$ expression ratios. Root mean squared difference between each pair is about 0.4.
Figure 13:
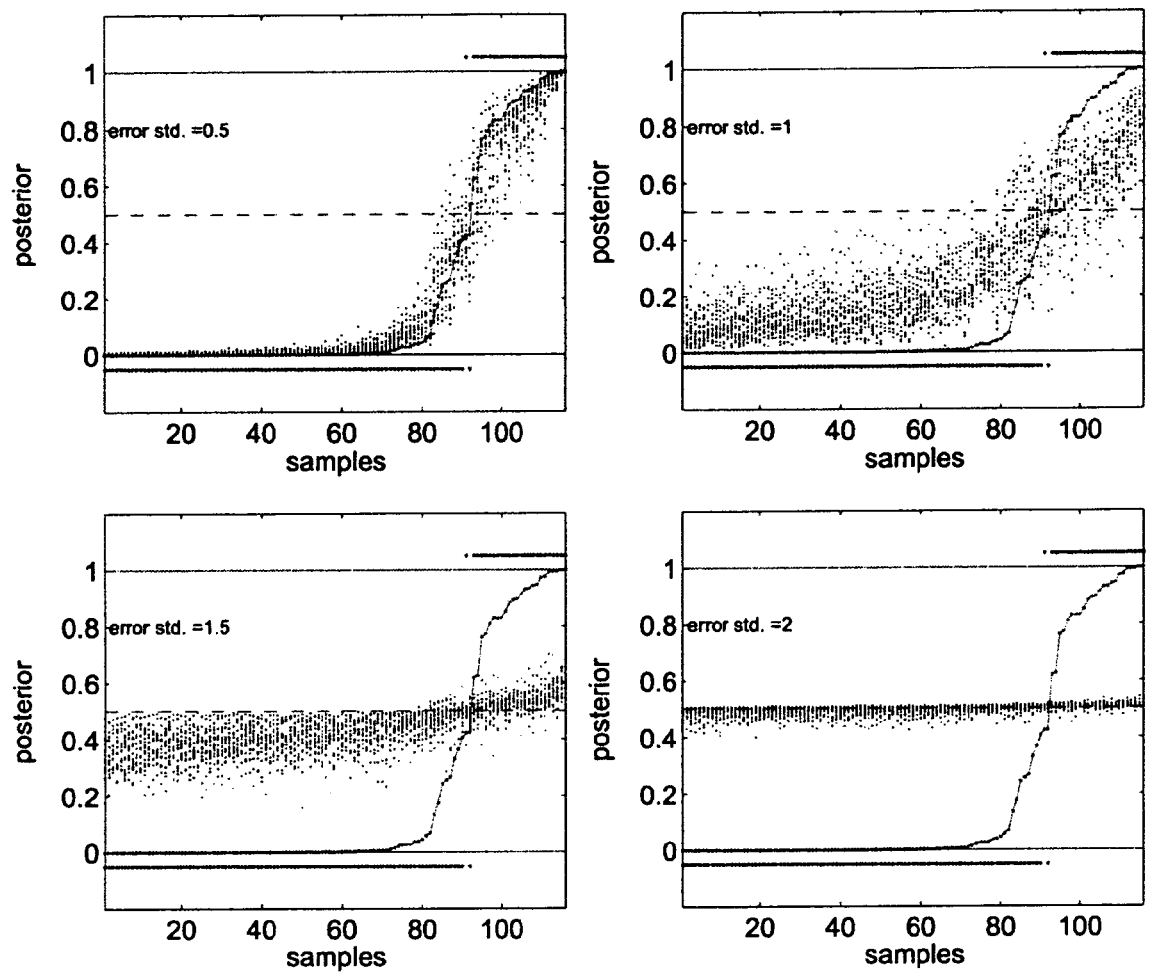
FIG. 13 shows posterior variation and robustness against artificially added Gaussian noise. In each panel, the vertical axis denotes the posterior value and the horizontal axis denotes the samples sorted in order of the original (without noise) posterior value (green). For each sample, posterior was calculated 20 times by adding Gaussian noise with 4 types of std.: 0.5, 1.0, 1.5 and 2.0, where std.=1 means that the noise scale is as large as the standard deviation of the original log expression ratio. Red points denote answers and blue points denote posterior in the 20 trials. Posterior value y denotes the probabilistic prognosis prediction, where its binarized y<0.5 or y>0.5 means that the sample is predicted as favorable or unfavorable, respectively, and when y is around 0.5, the prediction is supposed as unconfident. The original posterior values (green) are y<0.5 for patients whose prognosis is actually favorable, and y>0.5 for actually unfavorable. When noise with std.=0.5 is added (upper right panel), each posterior value (a small blue dot) changes from its original posterior (green). However, it rarely goes over the y=0.5 line, especially when the classifier is originally confident of the prediction, which indicates the robustness of the guess against the additional noise. When noise gets further large, the posterior values approach y=0.5 but their binarization seldom leads to wrong guess. In addition, when noise is extremely large and the gene expression shows a different pattern with those of the given samples, our supervised classifier outputs an unconfident posterior (lower right panel). Such a feature makes the prediction reliable like when applied in the clinical field.

As far as the inventors know, there have been only several reports of microarray analysis to predict the cancer prognosis in a similar way to this report. van't Veer et al. (Nature 415, 530-6 (2002)) have recently applied supervised classification to a breast cancer signature predictive of a short interval to distant metastases in the 78 patients initially without local lymph node metastasis. Their cross-validation analysis chose 70 genes as a classifier which predicted correctly the actual outcome of disease for 65 out of the 78 patients (83%). Singh et al. (Cancer Cell 1, 203-9 (2002)) used microarray expression analysis for determining genes predictive of the prognosis of prostate cancers using 52 patients. While no single gene was statistically correlated with recurrence, a 5-gene model with 2 nearest neighbors reached 90% accuracy in predicting recurrence during leave-one-out cross-validation. Ye et al. (Nat Med 9, 416-23 (2003)) also predicted metastasis and survival of hepatocellular carcinoma using metastasis predictor model with 20 samples for training and the other 20 for testing. Their supervised machine learning algorithm identified 153 significant genes. These reports have suggested the feasibility of microarray as a diagnostic tool in the clinic in some focused issues such as metastasis or recurrence. In contrast to these analyses, in the present study, the inventors have not selected the tumor subsets but included all 136 tumor samples randomly picked up from the tissue bank which have been collected from the hospitals all over Japan and treated under the control of therapeutic protocols proposed by the group study. The accuracy by the GP classifier determined 70 genes as the best number by the cross-validation technique. When the 87 training samples are evaluated by the cross-validation, the accuracy is 87%. More strikingly, the prognosis for the 29 new test samples is correctly predicted by 93% (27/29) that is extremely high as compared with those reported previously (van't Veer et al., 2002; Singh et al., 2002; Ye et al., 2003). One of the two tumors apparently misdiagnosed (S081 in FIG. 3) shows the posterior value of 0.86 but the patient is alive for 62 months after diagnosis. However, since the primary tumor of this patient is in stage 3 and shows low levels of TrkA expression, it may still have a possibility to recur after a further long time follow-up. In addition to the high accuracy, the method of this invention has a practical advantage to choose a suitable therapeutic protocol. In fact, the outcome prediction is almost perfect when the posterior value is large enough (unfavorable) or small enough (favorable) (FIGS. 3 and 4). Moreover, it is found that the probabilistic output by the GP classifier, as posterior, is very stable under the existence of noise. Even when artificial noise whose variance is as large as the estimated noise variance of microarray is added to the expression profile data, the prognosis prediction does not degrade very much (FIG. 13). This robustness is confirmed when the noise variance goes up to 1.0 which is larger enough than the actual reproduction noise level 0.6 (FIGS. 10-12). Although the prediction confidence, represented by the posterior, decays as the noise level increases, this feature is suitable for clinical applications, because the uncertain prediction reflects the large noise possibly involved on the microarray. Thus, the present results suggest that the microarray system in this invention is extremely powerful to predict the prognosis of neuroblastoma.

The high outcome predictability of the system in this invention may be due to multiple reasons. The quality of the tumor samples is high since the system of neuroblastoma tissue bank has been established and handling of tumor tissues is rather uniform in every hospital with obtaining informed consent. The array with application of a new apparatus installed a piezo micro ceramic pump, gives highly quantitative as well as reproducible signals. The non-contact spotting method makes the spot shape almost a perfect circle. As a result, the spot excels in signal uniformity. In addition, the inventors introduced kernel-based supervised classification and selected top-scored 70 genes to predict the prognosis by decision of majority, or vote. The two-fold feature extraction, the gene selection based on the pair-wise correlation method and extracting the low-dimensional gene expression similarity by the Gaussian kernel, makes the classifier robust against noise involved in the test samples. Though the inventors did not perform microdissection of the parts of the tumor, it is already known that, in neuroblastoma, the stromal components such as Schwannian cells are very important to characterize the tumor's biology (for review, see Ambros, I. M. & Ambros, P. F. Eur J Cancer 4, 429-34 (1995); Ambros, I. M. & Ambros, P. F. Neuroblastoma, 229-243 (2000)). Thus, a good combination or choice of those procedures may have given a high level of the outcome predictability.

The gene with the highest score is tubulin alpha (TUBA1), which has never been reported as a prognostic factor in neuroblastoma. Its prognostic significance has also been confirmed by RT-PCR in primary tumors. High expression of TUBA1 in neuronal cells is associated with axonal outgrowth during development as well as axonal degeneration after axotomy in adult animal (Knoops, B. & Octave, J. N. Neuroreport 8, 795-8 (1997)). Its family gene, TUBA3, is also ranked in the top 70. Expression of TUBA3 is reported to be restricted to the adherent, morphologically differentiated neuronal and glial cells (Hall, J. L. & Cowan, N. J. Nucleic Acid Res 13, 207-23 (1985)). DDX1 gene, which is frequently co-amplified with MYCN in advanced neuroblastomas (Godbout, R. & Squire, J. Proc Natl Acad Sci USA 90, 7578-82 (1993) ; Noguchi, T. et al. Genes Chromosomes Cancer 15, 129-33 (1996)), is also ranked at higher score than MYCN. This may be concordant with the previous reports that MYCN mRNA expression is a weaker prognostic marker than its genomic amplification (Slavc, I. et al. Cancer Res 50, 1459-63 (1990)). The another important prognostic factor, TrkA, is not included in the top 70 genes but in the 120, probably because of its relatively low levels of mRNA expression as compared with those of the other genes. The prognostic influence of TrkA expression may be compensated by the other genes affected or regulated by a TrkA intracellular signaling. Notably, the log-rank test of each gene shows that 54 out of 70 genes have the p-value with less than 0.05 on the microarray when used the 136 primary neuroblastomas (Table 1) indicating that the inventors have identified a large number of genes which can be significant predictors of the outcome. Indeed, the significance of most of those genes as prognostic factors has been confirmed by using semi-quantitative RT-PCR. As for the expression profile of the 70 genes, it is relatively heterogeneous, since the inventors have chosen them by supervised classification but not by the pattern of expression profiling. Nevertheless, the poor-prognostic tumors show a typical pattern of differential expression in the selected genes. Of interest, a part of the intermediate type of neuroblastomas with poor outcome also shows a similar pattern, suggesting that the tumors with aggressive potential can be predictive. On the other hand, the clustering pattern of neuroblastomas in favorable stages is rather heterogeneous, which may be due to the mixed populations with different stages of differentiation and programmed cell death of the tumor cells.

The ROC curves (FIG. 7) clearly show that microarray alone can be the most powerful prognostic indicator among the prognostic factors. Furthermore, they have shown that the combination of microarray with age, stage and MYCN amplification should give a confident prediction of prognosis in neuroblastoma at the bedside. The posterior value will help the decision of therapeutic way, and the outcome prediction based on the posterior value is extremely robust to possible noise. Thus, application of the highly qualified cDNA microarray into the clinic may give a reality leading to a tailored medicine to enable better treatment of the cancer patients.

INDUSTRIAL APPLICABILITY

As explained in detail above, according to the invention of this application, it becomes possible to predict the postoperative prognosis of a patient with neuroblastoma with extreme convenience and high accuracy. An accurate prediction will be able to eliminate excess medical treatment for a good prognosis patient, and to give sufficient medical treatment to a patient who is suspected of poor prognosis. Therefore, the invention of this application is extremely useful in industrial fields related to medical practices.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07601532B2). An electronic copy of the "Sequence Listing" will also be available from the USPTO upon request and payment of the fee set forth in 37 CFR 1.19(b)(3).

We claim:
1. A microarray, comprising:
a first combination of 25 different probes respectively comprising the sequences set forth in SEQ ID NOs: 5, 14, 16, 17, 22, 23, 28, 37, 51, 64, 67, 87, 113, 129, 132, 136, 142, 152, 155, 163, 165, 171, 173, and 191, and full-length complementary sequences thereof, and
a second combination of 25 different probes respectively comprising the sequences set forth in SEQ ID NOs:2, 4, 7, 13, 18, 20, 25, 26, 34, 38, 42, 46, 55, 70, 79, 83, 86, 92, 105, 114, 119, 124, 172, 179, and 183, and full-length complementary sequences thereof.

* * * * *